US010327666B2

(12) United States Patent
Lachaine et al.

(10) Patent No.: US 10,327,666 B2
(45) Date of Patent: Jun. 25, 2019

(54) MAGNETIC RESONANCE PROJECTION IMAGING

(71) Applicant: Elekta, Inc., Atlanta, GA (US)

(72) Inventors: Martin Emile Lachaine, Montreal (CA); Tony Falco, La Prairie (CA)

(73) Assignee: Elekta, Inc., Atlanta, GA (US)

(*) Notice: Subject to any disclaimer, the term of this patent is extended or adjusted under 35 U.S.C. 154(b) by 16 days.

(21) Appl. No.: 15/534,328

(22) PCT Filed: Dec. 10, 2015

(86) PCT No.: PCT/US2015/065014
§ 371 (c)(1),
(2) Date: Jun. 8, 2017

(87) PCT Pub. No.: WO2016/094668
PCT Pub. Date: Jun. 16, 2016

(65) Prior Publication Data
US 2017/0361128 A1     Dec. 21, 2017

Related U.S. Application Data

(60) Provisional application No. 62/090,115, filed on Dec. 10, 2014.

(51) Int. Cl.
*A61N 5/10*     (2006.01)
*G01R 33/483*     (2006.01)
(Continued)

(52) U.S. Cl.
CPC ............ *A61B 5/055* (2013.01); *A61N 5/1037* (2013.01); *A61N 5/1045* (2013.01);
(Continued)

(58) Field of Classification Search
CPC ...... A61B 5/055; G16H 30/40; A61N 5/1037; A61N 5/1045; A61N 5/1049;
(Continued)

(56) References Cited

U.S. PATENT DOCUMENTS 6,708,054 B2    3/2004    Shukla et al.
2006/0074292 A1    4/2006    Thomson et al.
(Continued)

FOREIGN PATENT DOCUMENTS

AU    2015360491 A1    7/2017
CN    101005874 A    7/2007
(Continued)

OTHER PUBLICATIONS

"International Application Serial No. PCT/US2015/065014, International Search Report dated Mar. 10, 2016", 6 pgs.
(Continued)

*Primary Examiner* — Nicole M Ippolito
(74) *Attorney, Agent, or Firm* — Schwegman Lundberg & Woessner, P.A.; Sanjay Agrawal

(57) ABSTRACT

Apparatus and techniques are described herein for nuclear magnetic resonance (MR) projection imaging. Such projection imaging may be used to control radiation therapy delivery to a subject, such as including receiving reference imaging information, generating a two-dimensional (2D) projection image using imaging information obtained via nuclear magnetic resonance (MR) imaging, the 2D projection image corresponding to a specified projection direction, the specified projection direction including a path traversing at least a portion of an imaging subject, determining a change between the generated 2D projection image and the reference imaging information, and controlling delivery of the radiation therapy at least in part using the determined change between the obtained 2D projection image and the reference imaging information.

20 Claims, 10 Drawing Sheets

(51) Int. Cl.
*G01R 33/56* (2006.01)
*G06T 7/00* (2017.01)
*G06K 9/46* (2006.01)
*G01R 33/567* (2006.01)
*A61B 5/055* (2006.01)
*G01R 33/48* (2006.01)
*G01R 33/563* (2006.01)
*G06T 11/00* (2006.01)
*G06F 19/00* (2018.01)
*G16H 30/40* (2018.01)
*A61B 6/00* (2006.01)
*G01R 33/565* (2006.01)

(52) U.S. Cl.
CPC ......... *A61N 5/1049* (2013.01); *A61N 5/1067* (2013.01); *G01R 33/4824* (2013.01); *G01R 33/4833* (2013.01); *G01R 33/567* (2013.01); *G01R 33/5608* (2013.01); *G01R 33/56308* (2013.01); *G06F 19/00* (2013.01); *G06K 9/46* (2013.01); *G06T 7/0012* (2013.01); *G06T 11/005* (2013.01); *G16H 30/40* (2018.01); *A61B 6/5229* (2013.01); *A61N 2005/1055* (2013.01); *A61N 2005/1061* (2013.01); *G01R 33/56325* (2013.01); *G01R 33/56509* (2013.01); *G06T 2207/10088* (2013.01); *G06T 2207/10116* (2013.01)

(58) Field of Classification Search
CPC .............. A61N 5/1067; G01R 33/4824; G01R 33/4833; G01R 33/5608; G01R 33/56308; G01R 33/567; G06F 19/00; G06K 9/46; G06T 7/0012; G06T 11/005
USPC ........................................... 250/492.1, 492.3
See application file for complete search history.

(56) References Cited

U.S. PATENT DOCUMENTS

| | | |
|---|---|---|
| 2007/0159174 A1 | 7/2007 | Oshio |
| 2009/0143669 A1 | 6/2009 | Harms et al. |
| 2010/0239153 A1 | 9/2010 | Kuduvalli et al. |
| 2012/0008734 A1* | 1/2012 | Thomson ............... G06T 7/0014 378/4 |
| 2012/0245453 A1 | 9/2012 | Tryggestad et al. |
| 2013/0044863 A1 | 2/2013 | Lagendijk et al. |
| 2013/0197347 A1 | 8/2013 | Moghari et al. |
| 2013/0261430 A1 | 10/2013 | Uhlemann et al. |
| 2013/0274539 A1 | 10/2013 | Yamada et al. |
| 2013/0336450 A1 | 12/2013 | Kyriakou et al. |
| 2014/0275962 A1* | 9/2014 | Foo ........................ A61N 2/002 600/411 |
| 2014/0296702 A1 | 10/2014 | Griswold et al. |
| 2018/0256064 A1* | 9/2018 | Lachaine ................ G06F 19/00 |

FOREIGN PATENT DOCUMENTS

| | | |
|---|---|---|
| CN | 101015723 A | 8/2007 |
| CN | 101076282 A | 11/2007 |
| CN | 103269752 A | 8/2013 |
| CN | 103460245 A | 12/2013 |
| CN | 103517737 A | 1/2014 |
| CN | 107106867 A | 8/2017 |
| CN | 107206251 A | 9/2017 |
| RU | 2355305 C1 | 3/2009 |
| RU | 2007132466 A | 3/2009 |
| RU | 2658135 C1 | 6/2018 |
| WO | WO-0114901 A1 | 3/2001 |
| WO | WO-2008099880 A1 | 8/2008 |
| WO | WO-2014016808 A1 | 1/2014 |
| WO | WO-2016094668 A1 | 6/2016 |
| WO | WO-2016094695 A1 | 6/2016 |

OTHER PUBLICATIONS

"International Application Serial No. PCT/US2015/065014, Written Opinion dated Mar. 10, 2016", 8 pgs.
"International Application Serial No. PCT/US2015/065052, International Search Report dated Apr. 5, 2016", 4 pgs.
"International Application Serial No. PCT/US2015/065052, Written Opinion dated Apr. 5, 2016", 7 pgs.
Nishimura, Dwight G., "Principles of Magnetic Resonance Imaging", (Apr. 1996), 4 pgs.
"Australian Application Serial No. 2015360491, First Examiners Report dated Oct. 3, 2017", 4 pgs.
"International Application Serial No. PCT/US2015/065014, International Preliminary Report on Patentability dated Jun. 22, 2017", 10 pgs.
"International Application Serial No. PCT/US2015/065052, International Preliminary Report on Patentability dated Jun. 22, 2017", 9 pgs.
"Australian Application Serial No. 2015360423, First Examination Report dated Jan. 22, 2018", 3 pgs.
"European Application Serial No. 15820378.5, Response filed Mar. 1, 2018 to Communication pursuant to Rules 161(1) and 162 EPC dated Aug. 22, 2018", 18 pgs.
Lachaine, Martin Emile, et al., "European Application Serial No. 15817038.1, Response filed Mar. 12, 2018 to Communication pursuant to Rules 161(1) and 162 EPC dated Sep. 1, 2017", 33 pgs.
"Australian Application Serial No. 2015360423, Response filed Jun. 12, 2018 to First Examination Report dated Jan. 22, 2018", 12 pgs.
"Australian Application Serial No. 2015360491, Response filed Jun. 12, 2018 to First Examiners Report dated Oct. 3, 2017", 15 pgs.
"Australian Application Serial No. 2015360491, Response filed Aug. 13, 2018 to Second Examiners Report dated Jul. 24, 2018", 12 pgs.
"Australian Application Serial No. 2015360491, Second Examiners Report dated Jul. 24, 2018", 11 pgs.
"European Application Serial No. 15817038.1, Communication Pursuant to Article 94(3) EPC dated Jun. 21, 2018", 6 pgs.
"European Application Serial No. 15817038.1, Response filed Oct. 30, 2018 to Communication Pursuant to Article 94(3) EPC dated Jun. 21, 2018", 14 pgs.
"Russian Application Serial No. 2017124030, Office Action dated May 24, 2018", W/English Translation.
"Russian Application Serial No. 2017124030, Office Action dated Oct. 22, 2018", w/ English translation, 12 pgs.
"Russian Application Serial No. 2017124030, Response filed Aug. 24, 2018 to Office Action dated May 24, 2018", w/English claims, 14 pgs.
"Russian Application Serial No. 2017124030, Response filed Jan. 22, 2019 to Office Action dated Oct. 22, 2018", w o English claims, 7 pgs.
"Chinese Application Serial No. 201580067688.8, Office Action dated Apr. 3, 2019", w/ English Translation.
"Chinese Application Serial No. 201580067407.9, Office Action dated Apr. 12, 2019", w/ English Translation, 14 pgs.

* cited by examiner

MAGNETIC RESONANCE PROJECTION IMAGING

CLAIM OF PRIORITY

This application is a U.S. national stage application filed under 35 U.S.C. § 371 from International Application Serial No. PCT/US2015/065014, filed on Dec. 10, 2015, and published as WO 2016/094668 on Jun. 16, 2016, which application claims the benefit of priority of Lachaine et al., U.S. Provisional Patent Application Ser. No. 62/090,115 titled "MAGNETIC RESONANCE PROJECTION IMAGING," filed on Dec. 10, 2014, the benefit of priority of each of which is hereby presently claimed, and each of which applications and publication are hereby incorporated by reference herein in their entirety.

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, protons, ions, high-energy photons, and the like). The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

Generally, ionizing radiation in the form of a collimated beam is directed from an external radiation source toward a patient. Modulation of a radiation beam may be provided by one or more attenuators or collimators (e.g., a multi-leaf collimator). The intensity and shape of the radiation beam may be adjusted by collimation avoid damaging healthy tissue (e.g., OARs) adjacent to the targeted tissue by conforming the projected beam to a profile of the targeted tissue.

The treatment planning procedure may include using a three-dimensional image of the patient to identify the target region (e.g., the tumor) and such as to identify critical organs near the tumor. Creation of a treatment plan may be a time consuming process where a planner tries to comply with various treatment objectives or constraints (e.g., dose volume histogram (DVH) objectives or other constraints), such as taking into account importance (e.g., weighting) of respective constraints in order to produce a treatment plan that is clinically acceptable. This task may be a time-consuming trial-and-error process that is complicated by the various organs at risk (OARs) because as the number of OARs increases (e.g., about thirteen for a head-and-neck treatment), so does the complexity of the process. OARs distant from a tumor may be more easily spared from radiation, but OARs close to or overlapping a target tumor may be more difficult to spare from radiation exposure during treatment.

Generally, for each patient, an initial treatment plan may be generated in an "offline" manner. The treatment plan may be developed well before radiation therapy is delivered, such as using one or more medical imaging techniques. Imaging information may include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor. The health care provider may delineate the target tumor that is to receive a prescribed radiation dose using a manual technique, and the health care provider may similarly delineate nearby tissue, such as organs, at risk of damage from the radiation treatment.

Alternatively or additionally, an automated tool (e.g., ABAS provided by Elekta AB, Sweden) may be used to assist in identifying or delineating the target tumor and organs at risk. A radiation therapy treatment plan ("treatment plan") may then be created using an optimization technique based on clinical and dosimetric objectives and constraints (e.g., the maximum, minimum, and mean doses of radiation to the tumor and critical organs).

The treatment planning procedure may include using a three-dimensional image of the patient to identify the target region (e.g., the tumor) and to identify critical organs near the tumor. Creation of a treatment plan may be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task may be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

The treatment plan may then be later executed by positioning the patient and delivering the prescribed radiation therapy. The radiation therapy treatment plan may include dose "fractioning," whereby a sequence of radiation therapy deliveries are provided over a predetermined period of time (e.g., 45 fractions or some other total count of fractions), such as with each therapy delivery including a specified fraction of a total prescribed dose. During treatment, the position of the patient or the position of the target region in relation to the treatment beam is important because such positioning in part determines whether the target region or healthy tissue is irradiated.

OVERVIEW

In one approach, nuclear magnetic resonance (MR) imaging may be combined with a radiation therapy system such as to provide imaging information to adapt or guide radiation therapy. An example of such a combined system may be referred to generally as "MRI-linac," comprising an MR imaging system, along with linear accelerator as a source of energy for radiation therapy. In an illustrative example, image acquisition may be performed just before initiation of delivery of a specified radiation therapy fraction. Such imaging may provide information helpful for identifying a position of a target region or for identifying motion of the target region. Such contemporaneous imaging may be referred to generically as "real-time," but in general a latency or time delay exists between an acquisition of an image and a delivery of radiation therapy.

The present inventors have recognized, among other things, that a problem exists in using 3D MR imaging to plan or adapt radiation therapy. For example, image reconstruction of an imaged volumetric region may be adversely affected when the target region is influenced by respiration or other motion, because the imaging duration ("imaging time") is generally long enough to be affected by such motion. In addition, an acquisition latency or a long acquisition duration may be problematic because the target region may have deformed or moved significantly between a 3D MR image acquisition and a later radiation therapy delivery.

In one approach, such as when target region motion is periodic, a four-dimensional MR imaging technique may be used such as prior to radiation treatment. For example, image acquisition may be synchronized to a physiologic cycle, such as by sensing surrogate information. Examples of surrogates include a signal sensed using a respiration belt or a one-dimensional (1D) navigator echo indicated by MR imaging. MR imaging elements, such as acquired imaging slices, may be sorted into bins using information indicative of a phase or amplitude of the physiologic cycle or a surrogate correlated with such a cycle. However, such an approach may also have limitations. For example, generally available slice-based 4D imaging techniques (such as non-projection MR imaging) do not include use of an anatomical landmark such as a diaphragm location to sort or bin acquired 3D images with respect to a physiologic cycle. Instead, generally available 4D imaging techniques acquire images sequentially and the acquired images contain different portions of the anatomy and lack common anatomical features across each image. By contrast, a projection imaging approach can include selecting or generating projection images having a common anatomical feature in each image so the common feature can be used to facilitate binning. Even if a different perspective of the feature is present in each of the projection images (e.g., different views of the feature), such feature tracking for binning can still be used in a projection imaging approach. In this manner, unlike generally-available 4D MR imaging techniques, a surrogate (such as an external surrogate) is not required.

Generally-used 4D MR imaging protocols also include relatively long acquisition times and may be time-prohibitive, such as in applications where updated imaging is to be performed prior to each radiation therapy treatment fraction. Also, 4D MR imaging techniques may not necessarily represent or predict an anatomical state of an imaging subject during a subsequent delivery of radiation therapy. For example, baseline drifts, deformations, or changes in frequency or phase of the physiologic cycle may occur between the time at which the 4D MR imaging information is acquired, and a later delivery of radiation therapy.

In another approach, imaging information indicative of intrafractional motion of the target region or other portions of the imaging subject may include imaging just a portion of the imaging subject, without requiring full volumetric imaging, such as by acquiring two-dimensional (2D) imaging slices, such as through the target region along different directions (such as including acquisition of a sequence of orthogonal slices). Such slices may be used to help localize the target region or other anatomy, generally, for delivery of radiation therapy. Such localization may be assisted in part using one or more of image segmentation or image registration techniques. However, such an approach may also have limitations. For example, MR imaging pulse sequences used to obtain 2D slices may be different than those used to obtain pre-treatment interfractional volumetric 3D or 4D "reference" imaging. Such different pulse sequences may make registration between 2D slices and an earlier-acquired volumetric reference image challenging. Another limitation is that out-of-slice information is lost, such as in an example where multiple organs-at-risk (OARs) are present or if retrospective dose calculations are to be made by acquiring imaging information during treatment. Yet another limitation of using 2D imaging slices is that it may be difficult to align slices with target motion, particularly if the motion varies between physiologic cycles such as between respiration cycles. Small targets such as tumors may be deformed or may disappear entirely from a particular acquired imaging slice.

The present inventors have recognized a solution to the limitations mentioned above. Such a solution may include using an MR projection imaging approach. Such a projection imaging approach may be used intrafractionally. Alternatively, or additionally, MR projection imaging may be used in a similar manner for simulation imaging to be used for treatment planning, or pre-treatment (e.g., "reference") imaging performed interfractionally to shift the patient or adapt the treatment plan prior to treatment delivery. Use of MR projection imaging for simulation imaging, pre-treatment reference imaging, and later intrafractional imaging may provide consistency and ease of registration or other processing. MR projection imaging may also provide imaging information in manner that more closely correlates with beam-eye-view (BEV) portal imaging or X-ray techniques, but without exposing the imaging subject to ionizing radiation during imaging. Obtaining 2D MR projection images may dramatically decrease imaging acquisition latency as compared to other approaches such as full 3D volumetric MR imaging, and 2D projection images may be aggregated such as to provide volumetric imaging information using tomographic or Fourier domain (k-space) techniques, for example. Information from acquired 2D MR projection images or from 3D or 4D imaging constructed from 2D MR projection images may be compared to reference imaging information, such as to localize a target region or anatomical landmarks, or to predict a later target region location. In this manner, information indicative of the target region may be used to adapt radiation therapy.

According to various examples, apparatus and techniques described herein may be used to control radiation therapy delivery to a subject using projection imaging techniques. For example, reference imaging may be received, such as including imaging information obtained earlier in relation to radiation therapy treatment planning. A two-dimensional (2D) projection image may be generated using imaging information obtained via nuclear magnetic resonance (MR) imaging, the 2D projection image corresponding to a specified projection direction, the specified projection direction including a path traversing at least a portion of an imaging subject. A change between the generated 2D projection image and the reference imaging information may be determined. Delivery of the radiation therapy may be controlled at least in part (e.g., in an adaptive manner) using the determined change between the obtained 2D projection image and the reference imaging information.

The present inventors have also recognized that reference imaging information may be obtained using projection imaging techniques, such as for use in spatially-registering later-obtained projection images with earlier-acquired imaging information. According to various examples, apparatus and techniques described herein may be used to generate four-dimensional (4D) or other imaging information, such as during one or more of obtaining reference images before radiation therapy (e.g., reference imaging), or later such as just before or during delivery of radiation therapy (e.g., intrafractional imaging). Generating the 4D imaging information may include generating two or more two-dimensional (2D) images, the 2D images comprising projection images representative of different projection angles, where the 2D images are generated using imaging information obtained via nuclear magnetic resonance (MR) imaging. Particular 2D images may be assigned to bins at least in part using information indicative of temporal positions within the physiologic cycle corresponding to the particular 2D images. Three-dimensional (3D) images may be constructed using the binned 2D images. A group of 3D images may be aggregated such as to provide 4D imaging information.

This overview is intended to provide an overview of subject matter of the present patent application. It is not intended to provide an exclusive or exhaustive explanation of the invention. The detailed description is included to provide further information about the present patent application.

Figure 1A:
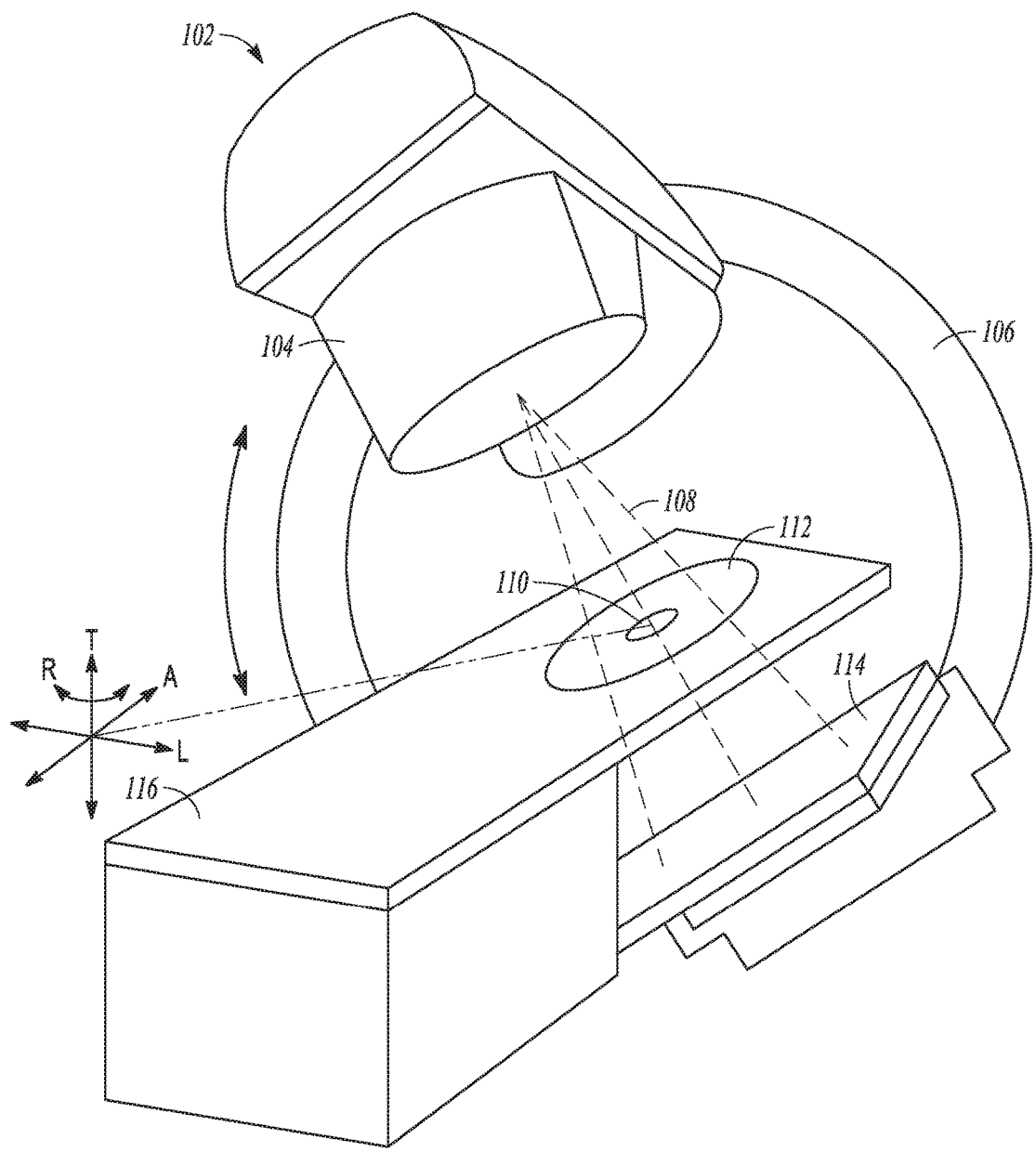
FIG. 1A illustrates generally an example of a radiation therapy system that may include radiation therapy output configured to provide a therapy beam.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A illustrates generally an example of a radiation therapy system 102 that may include radiation therapy output 104 configured to provide a therapy beam 108. The radiation therapy output 104 may include one or more attenuators or collimators, such as a multi-leaf collimator (MLC) as described in the illustrative example of FIG. 2. Referring back to FIG. 1A, a patient may be positioned in a region 112, such as on a platform 116 (e.g., a table or a couch), to receive a prescribed radiation therapy dose according to a radiation therapy treatment plan.

The radiation therapy output 104 may be located on a gantry 106 or other mechanical support, such as to rotate the therapy output 104 around an axis ("A"). One or more of the platform 116 or the radiation therapy output 104 may be moveable to other locations, such as moveable in transverse direction ("T") or a lateral direction ("L"). Other degrees of freedom are possible, such as rotation about one or more other axes, such as rotation about a transverse axis (indicated as "R").

The coordinate system (including axes A, T, and L) shown in FIG. 1A may have an origin located at an isocenter 110. The isocenter may be defined as a location where the radiation therapy beam 108 intersects the origin of a coordinate axis, such as to deliver a prescribed radiation dose to a location on or within a patient. For example, the isocenter 110 may be defined as a location where the radiation therapy beam 108 intersects the patient for various rotational positions of the radiation therapy output 104 as positioned by the gantry 106 around the axis A.

In an example, a detector 114 may be located within a field of the therapy beam 108, such as may include a flat panel detector (e.g., a direct detector or a scintillation-based detector). The detector 114 may be mounted on the gantry 106 opposite the radiation therapy output 104, such as to maintain alignment with the therapy beam 108 as the gantry 106 rotates. In this manner, the detector 114 may be used to monitor the therapy beam 108 or the detector may be used 114 for imaging, such as portal imaging of a projection of the beam 108 through the region 112. The region 112 may define a plane and a projection of the therapy beam 108 in the region 112 may be referred to as a "Beam Eye View" of the region 112.

In an illustrative example, one or more of the platform 116, the therapy output 104, or the gantry 106 may be automatically positioned, and the therapy output 104 may establish the therapy beam 108 according to a specified dose for a particular therapy delivery instance. A sequence of therapy deliveries may be specified according to a radiation therapy treatment plan, such as using one or more different orientations or locations of the gantry 106, platform 116, or therapy output 104. The therapy deliveries may occur sequentially, but may intersect in a desired target region on or within the patient, such as at the isocenter 110. A prescribed cumulative dose of radiation therapy may thereby be delivered to the target region while damage to tissue nearby the target region, such as one or more organs-at-risk, is reduced or avoided.

As mentioned in relation to other examples herein, the radiation therapy system 102 may include or may be coupled to an imaging acquisition system, such as to provide one or more of nuclear magnetic resonance (MR) imaging, or X-ray imaging, such as may include computed tomography (CT) imaging. In an example, MR imaging information or other imaging information may be used to generate imaging information or visualizations equivalent to CT imaging, without requiring actual CT imaging. Such imaging may be referred to as "pseudo-CT" imaging.

Figure 1B:
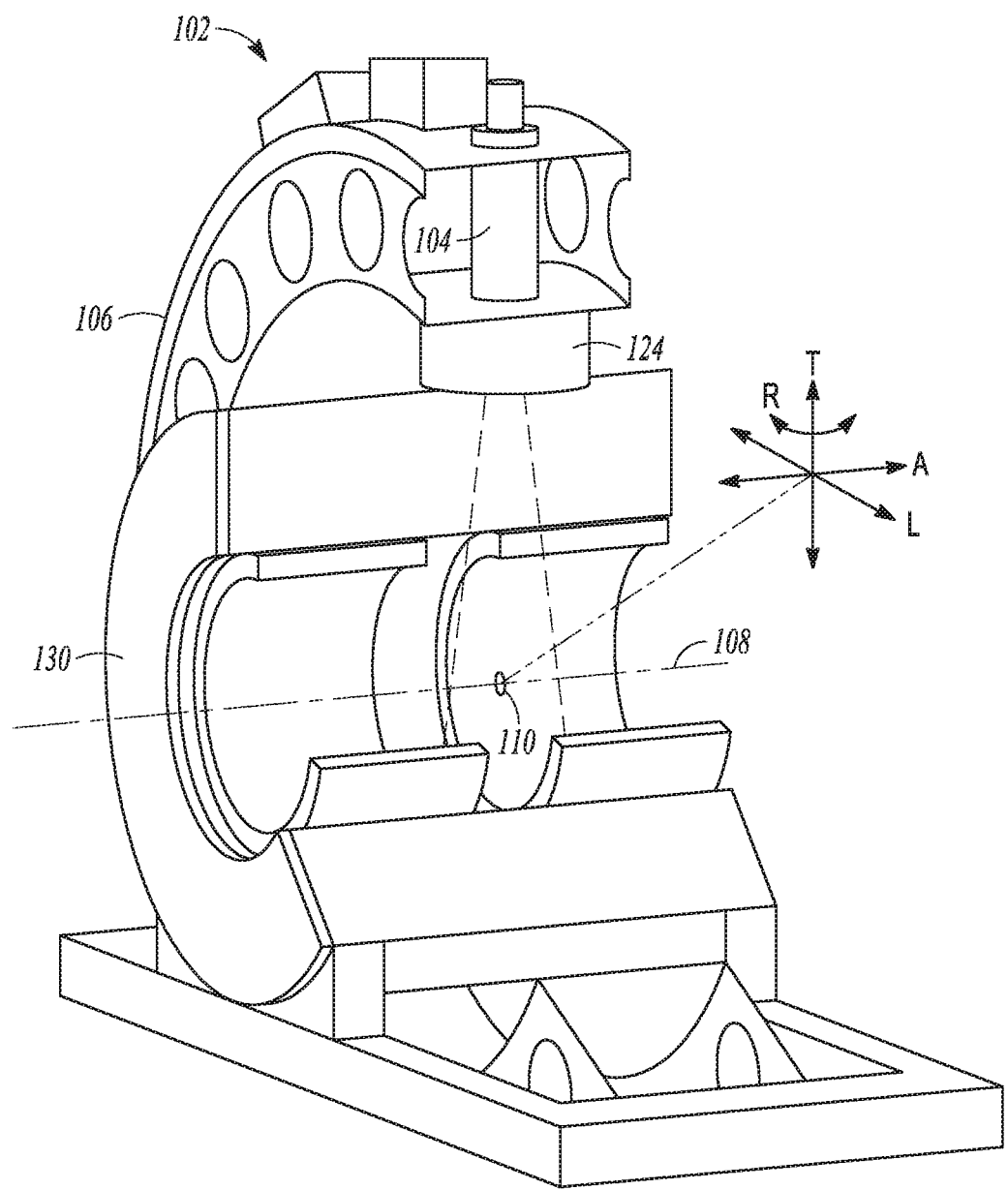
FIG. 1B illustrates generally a partially cut-away view of an example of a system that including a combined radiation therapy system and a nuclear magnetic resonance (MR) imaging system.

FIG. 1B illustrates generally a partially cut-away view of an example of a system that including a combined radiation therapy system 102 and a nuclear magnetic resonance (MR) imaging system 130. The MR imaging system 130 may be arranged to define a "bore" around an axis ("A"), and the radiation therapy system may include a radiation therapy output 104, such as to provide a radiation therapy beam 108 directed to an isocenter 110 within the bore along the axis, A. The radiation therapy output 104 may include a collimator 124, such as to one or more of control or shape the radiation therapy beam 108 to direct the beam 108 to a target region within a patient. The patient may be supported by a platform, such as a platform positionable along one or more of an axial direction, A, a lateral direction, L, or a transverse direction, T. One or more portions of the radiation therapy system 102 may be mounted on a gantry 106, such as to rotate the radiation therapy output 104 about the axis A.

FIG. 1A and FIG. 1B illustrate generally examples including a configuration where a therapy output may be rotated around a central axis (e.g., an axis "A"). Other radiation therapy output configurations may be used. For example, a radiation therapy output may be mounted a robotic arm or manipulator, such as having multiple degrees of freedom. In yet another example, the therapy output may be fixed, such as located in a region laterally separated from the patient, and a platform supporting the patient may be used to align a radiation therapy isocenter with a specified target region within the patient.

Figure 2:
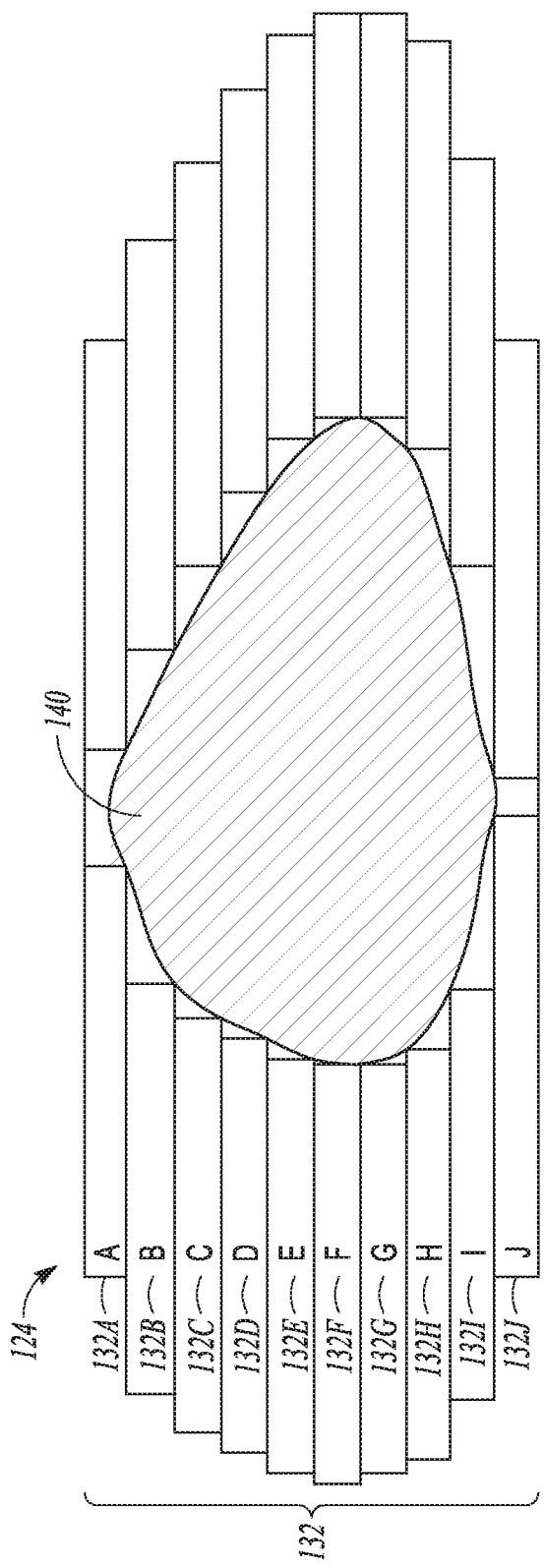
FIG. 2 illustrates generally an example of a collimator configuration, such as may be used in part to shape or collimate a radiation therapy beam.

FIG. 2 illustrates generally an example of a multi-leaf collimator (MLC) configuration 132, such as may be used in part to shape or collimate a radiation therapy beam. In FIG. 2, leaves 132A through 132J may be automatically positioned to define an aperture approximating a tumor 140 cross section or projection. The leaves 132A through 132J may be made of a material specified to attenuate or block the radiation beam in regions other than the aperture, in accordance with the radiation treatment plan. For example, the leaves 132A through 132J may include metallic plates, such as comprising tungsten, with a long axis of the plates oriented parallel to a beam direction, and having ends oriented orthogonally to the beam direction (as shown in the plane of the illustration of FIG. 2).

A "state" of the MLC 132 may be adjusted adaptively during a course of radiation therapy, such as to establish a therapy beam that better approximates a shape or location of the tumor 140 or other targeted region, as compared to using a static collimator configuration or as compared to using an MLC 132 configuration determined exclusively using an "offline" therapy planning technique. A radiation therapy technique including using the MLC 132 to produce a specified radiation dose distribution to a tumor or to specific areas within a tumor may be referred to as Intensity Modulated Radiation Therapy (IMRT). As described in relation to other examples herein, imaging may be performed to localize the target region or to determine or predict a perspective of a target region from the point-of-view of the radiation therapy beam to adaptively guide therapy.

Figure 3:
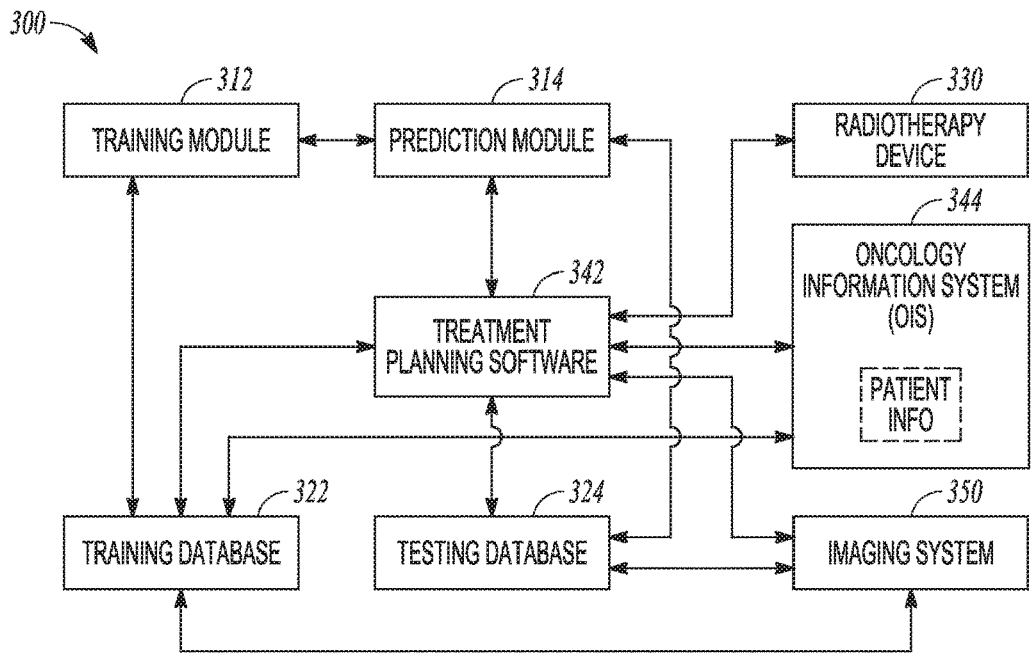
FIG. 3 illustrates generally an example of radiation therapy system, such as may include a radiation therapy device and an imaging acquisition device.

FIG. 3 illustrates generally an example of radiation therapy system 300, such as may include a radiation therapy device 330 and an imaging acquisition device. Radiation therapy system 300 may include a training module 312, a prediction module 314, a training database 322, a testing database 324, a radiation therapy device 330, and an image acquisition device 350. Radiation therapy system 300 may also be connected to a treatment planning system (TPS) 342 and an oncology information system (OIS) 344, which may provide patient information. In addition, radiation therapy system 300 may include a display device and a user interface.

Figure 4:
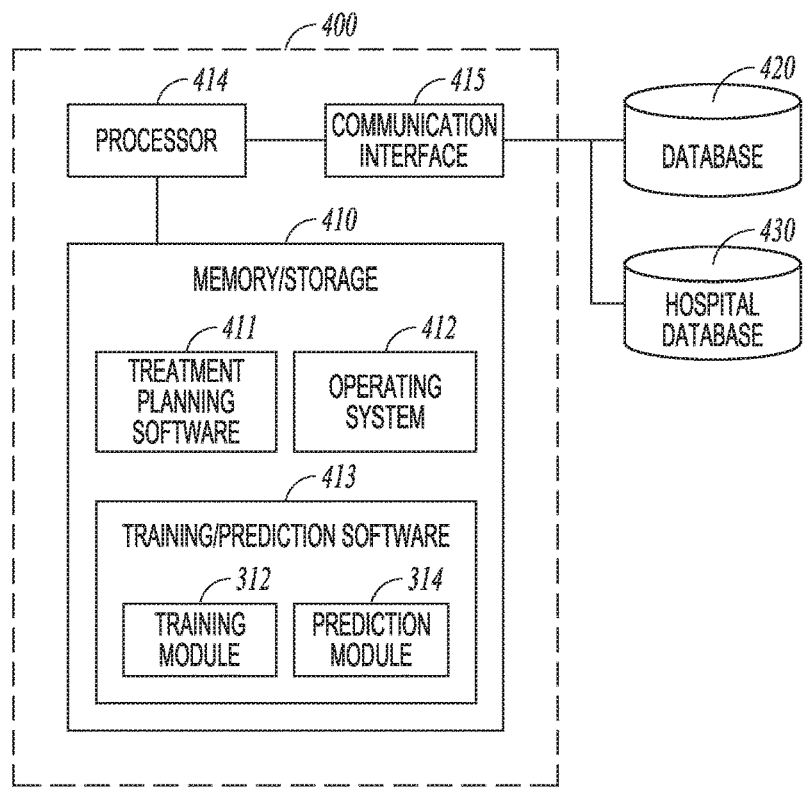
FIG. 4 illustrates generally an example of a system that may be used for one or more of imaging acquisition, image segmentation, target prediction, therapy control, or therapy adjustment.

FIG. 4 illustrates generally an example of a system 400 that may be used for one or more of imaging acquisition, image segmentation, target prediction, therapy control, or therapy adjustment. According to some embodiments, system 400 may be one or more high-performance computing devices capable of identifying, analyzing, maintaining, generating, or providing large amounts of data consistent with the disclosed embodiments. System 400 may be standalone, or it may be part of a subsystem, which in turn may be part of a larger system. For example, system 400 may represent distributed high-performance servers that are remotely located and communicate over a network, such as the Internet, or a dedicated network, such as a local area network (LAN) or a wide-area network (WAN). In some embodiments, system 400 may include an embedded system, imaging scanner (e.g., a nuclear magnetic resonance (MR) scanner or other scanner such as a computed tomography (CT) scanner), and/or touch-screen display device in communication with one or more remotely located high-performance computing devices.

In one embodiment, system 400 may include one or more processors 414, one or more memories 410, and one or more communication interfaces 415. Processor 414 may be a processor circuit, including one or more general-purpose processing devices such as a microprocessor, central processing unit (CPU), graphics processing unit (GPU), or the like. More particularly, processor 414 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets.

Processor 414 may also be one or more special-purpose processing devices such as an application specific integrated circuit (ASIC), a field programmable gate array (FPGA), a digital signal processor (DSP), a System-on-a-Chip (SoC), or the like. As would be appreciated by those skilled in the art, in some embodiments, processor 414 may be a special-purpose processor, rather than a general-purpose processor. Processor 414 may include one or more known processing devices, such as a microprocessor from the Pentium™ or Xeon™ family manufactured by Intel™, the Turion™ family manufactured by AMD™, or any of various processors manufactured by other vendors such as Oracle™ (e.g., a SPARC™-architecture processor). Processor 414 may also include graphical processing units manufactured by Nvidia™. The disclosed embodiments are not limited to any type of processor(s) otherwise configured to meet the computing demands of identifying, analyzing, maintaining, generating, and/or providing large amounts of imaging data or any other type of data consistent with the disclosed embodiments.

Memory 410 may include one or more storage devices configured to store computer-executable instructions used by processor 414 to perform functions related to the disclosed embodiments. For example, memory 410 may store computer executable software instructions for treatment planning software 411, operating system software 412, and training/prediction software 413. Processor 414 may be communicatively coupled to the memory/storage device 410, and the processor 414 may be configured to execute the computer executable instructions stored thereon to perform one or more operations consistent with the disclosed embodiments. For example, processor 414 may execute training/prediction software 413 to implement functionalities of training module 312 and prediction module 314. In addition, processor device 414 may execute treatment planning software 411 (e.g., such as Monaco® provided by Elekta) that may interface with training/prediction software 413.

The disclosed embodiments are not limited to separate programs or computers configured to perform dedicated tasks. For example, memory 410 may include a single program that performs the functions of the system 400 or multiple programs (e.g., treatment planning software 411 and/or training/prediction software 413). Additionally, processor 414 may execute one or more programs located remotely from system 400, such as programs stored in database 420, such remote programs may include oncology information system software or treatment planning software. Memory 410 may also store image data or any other type of data/information in any format that the system may use to perform operations consistent with the disclosed embodiments.

Communication interface 415 may be one or more devices configured to allow data to be received and/or transmitted by system 400. Communication interface 415 may include one or more digital and/or analog communication devices that allow system 400 to communicate with other machines and devices, such as remotely located components of system 400, database 420, or hospital database 430. For example, Processor 414 may be communicatively connected to database(s) 420 or hospital database(s) 430 through communication interface 415. For example, Communication interface 415 may be a computer network, such as the Internet, or a dedicated network, such as a LAN or a WAN. Alternatively, the communication interface 415 may be a satellite communications link or any form of digital or analog communications link that allows processor 414 to send/receive data to/from either database(s) 420, 430.

Database(s) 420 and hospital database(s) 430 may include one or more memory devices that store information and are accessed and managed through system 400. By way of example, database(s) 420, hospital database(s) 530, or both may include relational databases such as Oracle™ databases, Sybase™ databases, or others and may include non-relational databases, such as Hadoop sequence files, HBase, Cassandra or others. The databases or other files may include, for example, one or more of raw data from MR scans or CT scans associated with an imaging subject, such as for training or providing a reference image, MR feature vectors, MR projection imaging information, CT values, reduced-dimension feature vectors, pseudo-CT prediction model(s), pseudo-CT value(s), pseudo-CT image, DICOM data, etc. Systems and methods of disclosed embodiments, however, are not limited to separate databases. In one aspect, system 400 may include database(s) 420 or hospital database(s) 430. Alternatively, database(s) 420 and/or hospital database(s) 430 may be located remotely from the system 400. Database(s) 420 and hospital database(s) 430 may include computing components (e.g., database management system, database server, etc.) configured to receive and process requests for data stored in memory devices of database(s) 420 or hospital database(s) 430 and to provide data from database(s) 420 or hospital database(s) 430.

System 400 may communicate with other devices and components of system 400 over a network (not shown). The network may be any type of network (including infrastructure) that provides communications, exchanges information, or facilitates the exchange of information and enables the sending and receiving of information between other devices and/or components of system 400 over a network (not shown). In other embodiments, one or more components of system 400 may communicate directly through a dedicated communication link(s), such as a link (e.g., hardwired link, wireless link, or satellite link, or other communication link) between system 400 and database(s) 420 and hospital database(s) 430.

The configuration and boundaries of the functional building blocks of system 400 has been defined herein for the convenience of the description. Alternative boundaries may be defined so long as the specified functions and relationships thereof are appropriately performed. Alternatives (including equivalents, extensions, variations, deviations, etc., of those described herein) will be apparent to persons skilled in the relevant art(s) based on the teachings contained herein.

Figure 5:
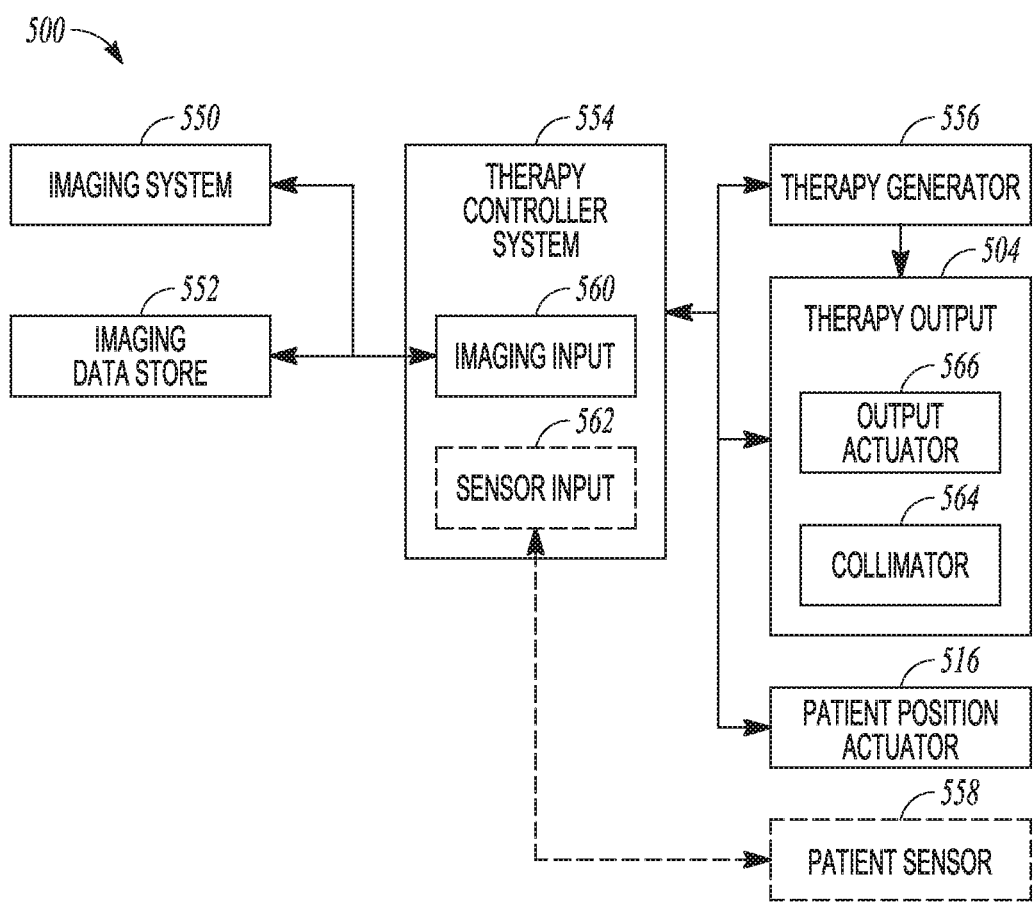
FIG. 5 illustrates generally an example of a system, such as may include a radiation therapy controller having an imaging input, a radiation therapy generator, and a radiation therapy output.

FIG. 5 illustrates generally an example of a system 500, such as may include a radiation therapy controller system 554 having an imaging input 560, a radiation therapy generator 556, and a radiation therapy output 504. The therapy generator 556 may include an accelerator, such as a linear accelerator, or another source of radiation, and the therapy output 504 may be coupled to the therapy generator 556 to process a beam of energetic photons or particles provided by the therapy generator 556. For example, the therapy output 504 may include or may be coupled to an output actuator 566 to one or more of rotate or translate the therapy output 504 to provide a radiation therapy beam directed to a desired target region. The therapy output 504 may include a collimator 564, such as a multi-leaf collimator as mentioned above in relation to FIG. 2. Referring back to FIG. 5, the therapy controller system 554 may be configured to control one or more of the therapy generator 556, the therapy output 504, or a patient position actuator 516 (such as a movable platform including a couch or table), using an adaptive radiation treatment technique as described in other examples herein.

The therapy controller system 554 may be coupled to one or more sensors, such as using a sensor input 562. For example, a patient sensor 558 may provide physiologic information to the therapy controller system, such as information indicative of one or more of respiration (e.g., using a plethysmographic sensor or respiration belt), patient cardiac mechanical or electrical activity, peripheral circulatory activity, patient position, or patient motion. Such information may provide a "surrogate" correlated with motion of one or more organs or other regions to be targeted by the therapy output 504. Such information may be used to control therapy such as for therapy gating or to assist in "binning" acquired imaging information according to one or more of a determined phase or amplitude range of a physiologic cycle as indicated by obtained information from the sensor 558.

The imaging input 560 may be coupled to an imaging system 550 (such as may include a computed tomography imaging system or a nuclear magnetic resonance (MR) imaging system, as illustrative examples). Alternatively, or in addition, the therapy controller system 554 may receive imaging information from an imaging data store 552, such as a centralized imaging database or imaging server. One or more of the therapy controller system 554 or the imaging system 550 may include elements shown and described in relation to the system 400 shown in FIG. 4.

Generally-available radiation therapy equipment can be used to acquire projection images using X-ray imaging techniques. For example, linear accelerator (linac) systems can acquire X-ray projection images using one or more of the megavoltage (MV) treatment beam itself combined with a portal imaging device (such as shown illustratively in FIG. 1A) or using one or more separate kilovolt (kV) X-ray sources. In an example, a kV X-ray source can be mounted on a gantry such as oriented at a 90-degree angle with respect to the treatment beam orientation. In another example, two independent X-ray source/imager pairs can be located to provide stereoscopic X-ray imaging. Projection images acquired using X-ray imaging represent a divergent X-ray path from the imaging source, which can be referred to as a "point source" or focal point.

Prior to delivery of radiation therapy, such as prior to a particular radiation therapy treatment fraction, X-ray computed tomography (CT) images may be acquired. For example, a cone-beam CT (CBCT) imaging technique can be used to obtain projection images at various projection angles during a rotation of a gantry-mounted X-ray source around an imaging subject. A three-dimensional (3D) image can be reconstructed from such cone beam projections. For imaging subjects that exhibit significant motion, such as respiratory motion, 3D CBCT images may be blurred because each projection may capture a snapshot of the patient at a different point in the respiration cycle or other physiologic cycle. To reduce motion blurring, four-dimensional (4D) CBCT imaging may be used, such as by binning projections according to a phase or amplitude of the physiologic cycle corresponding to the time at which the projection image was acquired.

The present inventors have recognized, among other things, that nuclear magnetic resonance (MR) imaging projections can be similarly acquired and processed, such as reducing exposure of the imaging subject to ionizing radiation and providing enhanced soft tissue contrast as compared to X-ray-based imaging approaches. The present inventors have also recognized, among other things, that MR projection images are not degraded by scattered radiation, and the projection imaging direction is not limited by physical constraints such as having to be oriented at 90 degrees relative to the treatment beam. MR projection imaging can be used to acquire a single imaging perspective (e.g., a 2D projection image) of all of the information contained within a depth extent of an excited imaging region, as opposed to using relatively thin 2D MR imaging slices which capture only a portion of the information in a depth direction. MR projection imaging does have limitations, such as that information in an acquired 2D projection image is not localized in the depth direction orthogonal to the projection imaging plane, and structures surrounding a targeted region can appear to partially mask it.

MR Projection Imaging Such as Using 1D Projection Lines

Figure 6:
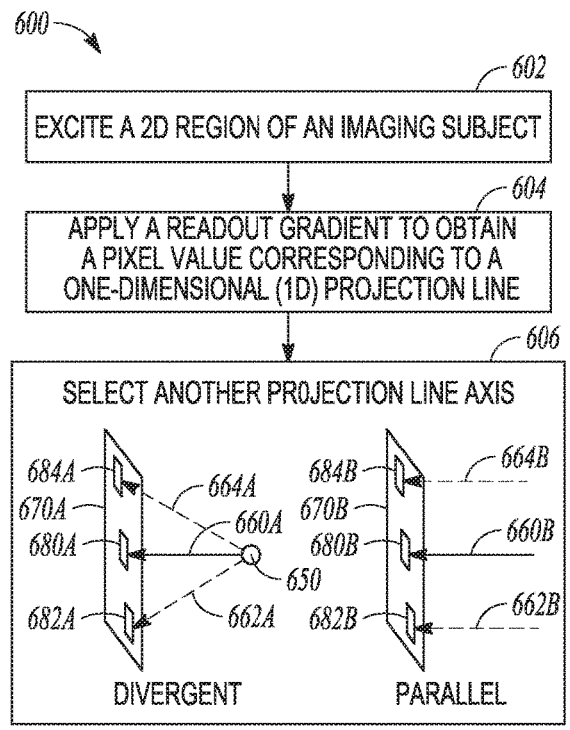
FIG. 6 illustrates generally a technique, such as a method, that may include using MR imaging to excite a region of an imaging subject, the region defining an imaging slice, and obtaining a pixel value corresponding to a one-dimensional projection line through the slice.

FIG. 6 illustrates generally a technique 600, such as a method, that may include at 602 using MR imaging to excite a region of an imaging subject. For example, a two-dimensional (2D) excitation sequence may be used. At 604, a readout gradient may be applied to the imaging subject, and a one-dimensional (1D) projection line (e.g., a "ray") through the 2D excited region may be acquired. At 606, another projection line axis may be selected, and a 2D region is again excited at 602, and a readout gradient is applied at 604 corresponding to the updated projection line axis. Referring to the inset diagrams at 606, the projection lines may be established in a divergent manner or a parallel manner. For example, if divergent projection line orientations are used, a resulting projection image defined in the plane 670A may provide a projection representation that is similar to projection images produced by divergent X-ray imaging techniques, or similar to a projection image produced by a radiation therapy output beam during portal imaging. In this manner, MR projection imaging can be used to simulate X-ray imaging, but with enhanced contrast and without undesired scattering, for example.

In the example of divergent MR projection imaging using 1D projection lines, the 1D projection lines can be specified to converge at a location 650, such as corresponding to a location of a radiation therapy beam source or corresponding to a location where an X-ray imaging source would generally reside. A scale and spatial resolution of information defined in a resulting 2D projection image established in the plane 670A may be determined by the distance between the source location 650 and a selected imaging plane 670A location. For example, a first projection line orientation 660A can be orthogonal to the projection imaging plane 670A, and a corresponding acquired 1D projection line can be used to establish a pixel value at a location 680A. All information acquired along the first projection line is generally incorporated and compressed into the pixel value, thus depth selectivity is lost in the direction along the projection line.

The line orientation 660A orthogonal to the projection imaging plane 670A may generally be referred to as the projection "direction" or "angle" even though in divergent examples, other projection line orientations are not parallel. A second projection line orientation 662A can similarly establish a second pixel value at a location 682A, and a third projection line orientation 664A can similarly establish a third pixel value at a location 684A. In a reconstructed image, the pixel locations 680A, 682B, and 684B are determined at least in part by a specified separation between the plane 670A location and the source location 650. To achieve higher spatial resolution in a lateral direction in plane 670A, a greater number of separate 1D projection line directions can be acquired at the cost of total 2D projection image acquisition duration, because particular acquired 1D projections are aggregated to create a full 2D projection in the plane 670A.

In a parallel 1D projection line example, such as at 606, a first projection line orientation 660B can be established to provide a first pixel value at a location 680B in a resulting projection image defined in the plane 670B. Other parallel lines 662B and 664B can be used to provide information for corresponding location 682B and 684B in the projection image. As a practical consideration, if exclusively parallel 1D projection lines are being used to construct a particular 2D projection image, the techniques of FIG. 7A or FIG. 7B may provide enhanced efficiency as compared to the example of FIG. 6 because a 2D projection image can be reconstructed directly by suppressing a slice selection gradient or by using a large slice thickness (relative to a depth extent of interest) without requiring excitation and readout of particular 1D projection lines.

Parallel projection can provide one or more of a simplified geometry compared to a divergent approach, one-to-one correspondence between projection image pixels and a plane defining a "beam eye view," or easier tomographic reconstruction from multiple projections. By comparison, X-ray-based CBCT tomographic reconstruction is generally only approximate due to divergence of the acquired cone-beam projection images. In either the divergent or parallel 1D projection line examples, the spacing or orientation of the projection lines need not be uniform and may be specified depending on a variety of factors. For example, a spatial resolution in a direction of predicted motion of a target within the field of view of the projection image and parallel to the projection image plane may be enhanced by increasing a spatial frequency of projection lines in the direction of predicted motion. Similarly, shorter total acquisitions can be provided by using a more sparse set of divergent projection lines.

Figure 7A:
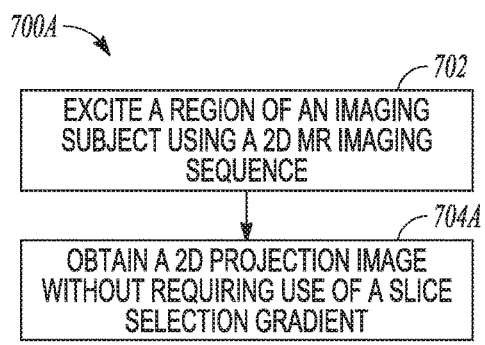
FIG. 7A illustrates generally a technique, such as a method, that may include exciting a region of an imaging subject using a two-dimensional (2D) MR imaging excitation sequence
Figure 7B:
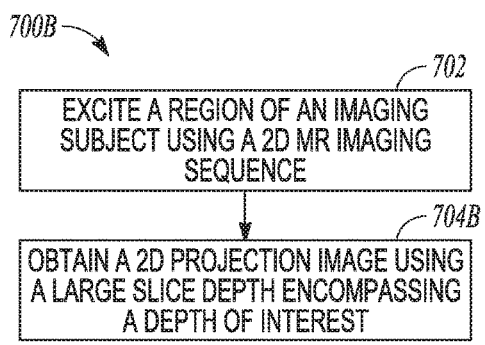
FIG. 7B illustrates generally another technique, such as a method, that may include exciting a region of an imaging subject using a two-dimensional (2D) MR imaging excitation sequence.

MR Projection Imaging Such as Using 2D Excitation without Requiring Slice Selection Gradient or Using Large Slice Depth Encompassing a Depth of Interest FIG. 7A illustrates generally a technique 700A, such as a method, that may include exciting a region of an imaging subject using a two-dimensional (2D) MR imaging excitation sequence at 702. FIG. 7B illustrates generally another technique 700B, such as a method, that may also include exciting a region of an imaging subject using a two-dimensional (2D) MR imaging excitation sequence at 702.

In the example of FIG. 7A, a 2D MR projection image can be obtained at 704A by using a 2D imaging sequence without requiring use of a slice selection gradient (e.g., the slice selection gradient pulse sequence can be suppressed or omitted) so that information in a depth direction (e.g., in the projection imaging direction and perpendicular to a plane of a resulting projection image) is acquired at all depths within the excited region. Such an approach does not require excitation and gradient readout of 1D projection lines and can therefore reduce image acquisition duration as compared to a 1D projection approach in the case where parallel 1D projection lines are desired.

In the example of FIG. 7B, a 2D MR projection image can be obtained at 704B by using a 2D imaging sequence using a slice selection gradient defining a slice sufficiently large in depth to encompass a region of depth of interest, such as corresponding to a portion or an entirety of a radiation therapy target extent in a dimension parallel to the projection angle. As the slice thickness is increased, the depth dimension of the slice includes more and more anatomical contribution of information that was previously out-of-field in depth. Such depth information is compressed into a single point or pixel location in the resulting 2D projection image. The technique 700B of FIG. 7B similarly offers a reduced image acquisition duration as compared to the 1D projection approach and can be referred to as a "very thick slice" projection approach.

MR imaging data can also be obtained in "k-space," representing a coordinate space corresponding to the spatial Fourier transform of the imaging information. For example, MR imaging data can be naturally collected in k-space by varying image gradients; a particular combination of x, y and z gradients generally corresponds to a single point in k-space. By sequentially filling the points in k-space, an inverse Fourier Transform can then be applied to the k-space representation to generate an image. A 2D plane in k-space corresponds to a 2D projection in image space. Accordingly, a 2D projection can also be obtained by acquiring k-space points that lie in a plane in k-space, and generating a 2D inverse Fourier Transform on the plane in k-space (a k-space slice) to obtain a 2D projection in image space.

Figure 8A:
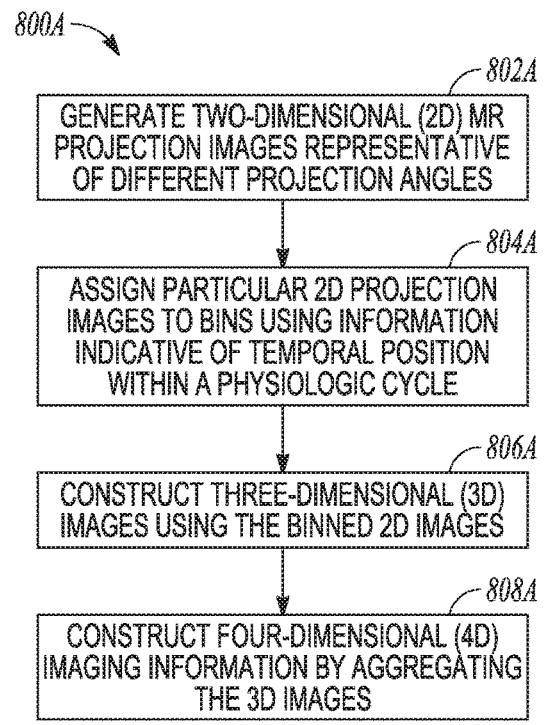
FIGS. 8A and 8B illustrate generally a technique, such as a method, that may include generating two-dimensional (2D) MR projection images representative of different projection angles, and using such 2D projection images to construct three-dimensional (3D) images.

Three-Dimensional (3D) and Four-Dimensional (4D) Imaging Using MR Projection Imaging Such as Correlated with a Physiologic Cycle FIG. 8A illustrates generally a technique 800A, such as a method, that may include generating two-dimensional (2D) MR projection images such as representative of different projection angles, and using such 2D projection images to construct three-dimensional (3D) images. A corresponding technique 800B is shown schematically in FIG. 8B.

Figure 8B:
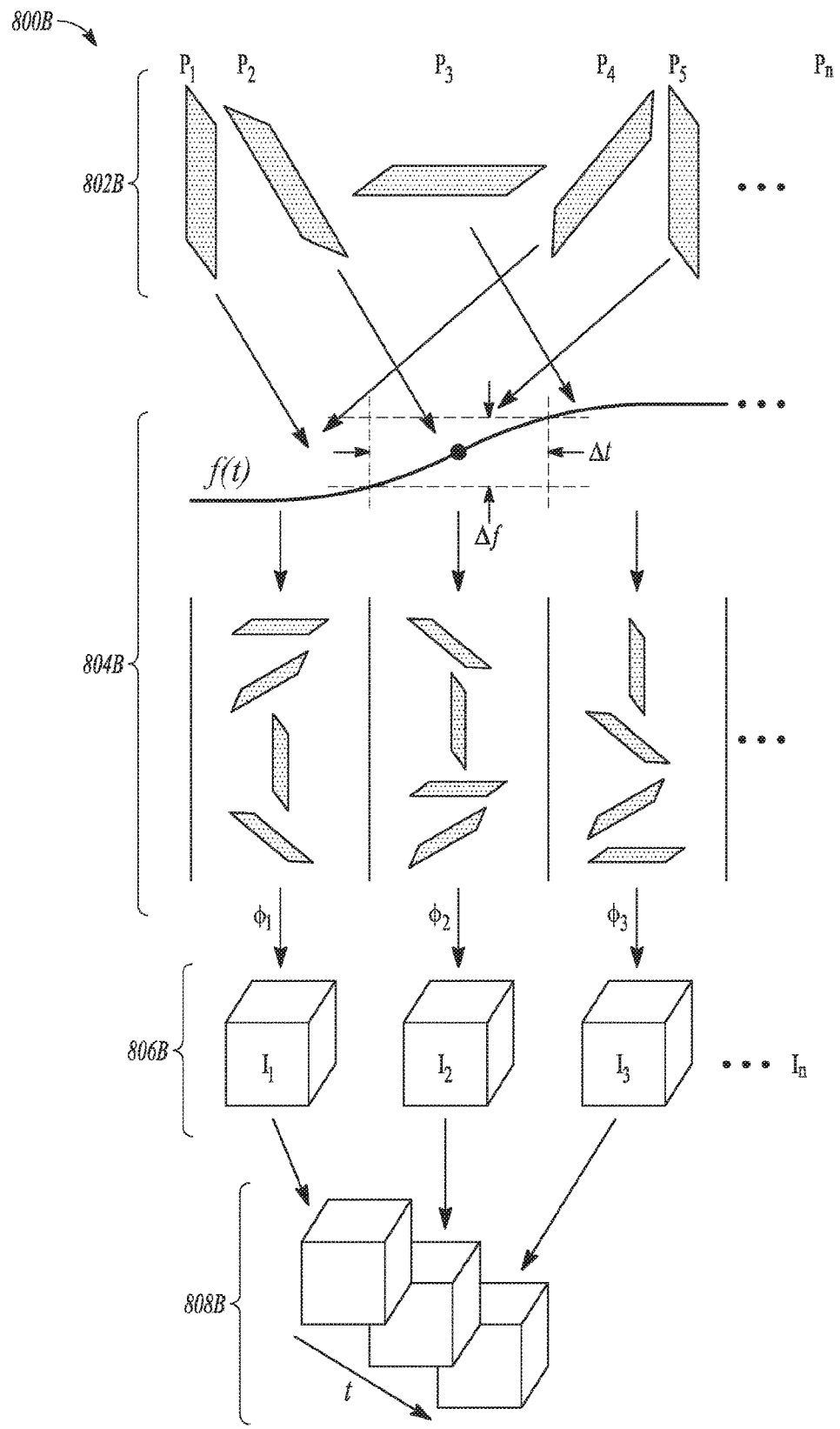

At 802A a series of 2D MR projection images can be generated, such as using one or more techniques mentioned elsewhere herein as shown, for example, in FIG. 6 (by aggregating 1D projection lines), or as shown in FIG. 7A or FIG. 7B. Referring to FIG. 8B at 802B, 2D projection images $P_1, P_2, P_3, \ldots, P_N$ can be acquired at different projection angles. For example, projection angles can be specified to capture projection directions around the imaging subject. Tomographic reconstruction may then be performed to obtain a 3D image. As the projection direction rotates around the patient, tomographic reconstruction techniques, such as similar to X-ray techniques including CT or CBCT reconstruction, can used to either create a new 3D image, or update a previous 3D image with new information.

However, motion may induce blurring in reconstructed 3D images. Accordingly, in FIG. 8A at 804A, particular acquired 2D projection images can be assigned to bins using information indicative of a temporal position within a physiologic cycle, such as respiration. Such binning can be accomplished using information obtained from one or more of a surrogate, an external marker, or an internal marker or feature. For example, to obtain information indicative of a respiration cycle, a respiration belt can be used to provide a surrogate signal or diaphragm motion can be tracked in acquired imaging information.

Referring to FIG. 8B, at 804B, f(t) can represent a plot of a signal representative of a portion of a physiologic cycle such as respiration. Various bins such as phase bins $\phi_1, \phi_2, \phi_3, \ldots, \phi_n$ can be established, such as corresponding to portions (e.g., a range $\Delta t$) along f(t). Acquired 2D projection images can be assigned to bins $\phi_1, \phi_2, \phi_3, \ldots, \phi_n$ such as by determining a portion of f(t) on which a particular acquired image falls. The use of phase-based bins is merely illustrative and amplitude bins could similarly be used, such as corresponding to amplitude ranges (e.g., a range $\Delta f$) along f(t).

Referring to FIG. 8A, at 806A a 3D image can be constructed using a binned series of 2D projection images corresponding to different projection angles. In the context of FIG. 8B, at 806B, the 3D images $I_1, I_2, I_3, \ldots, I_n$ can correspond to each of the bins $\phi_1, \phi_2, \phi_3, \ldots, \phi_n$. Referring to FIG. 8A, at 808A, 4D imaging information can be constructed by aggregating the 3D images constructed at 806A. In the context of FIG. 8B, the series of 3D images can provide a 4D representation of imaged region of the subject throughout the physiologic cycle. Motion induced by a physiologic cycle such as respiration may generally be highly periodic and reproducible.

MR Projection Imaging for Radiation Therapy Control

Figure 9:
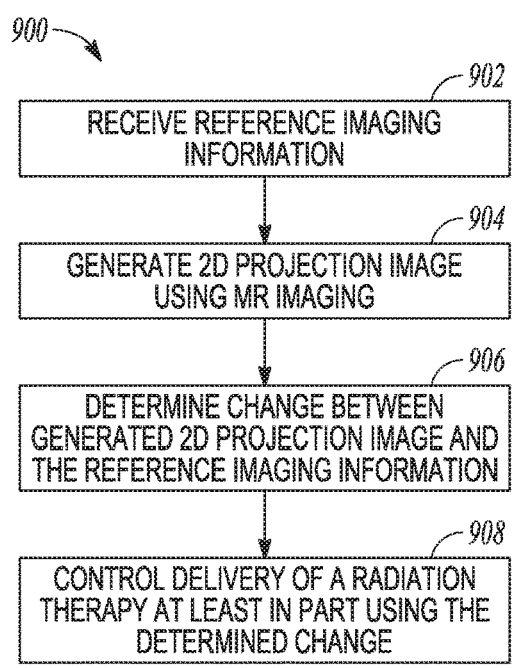
FIG. 9 illustrates generally a technique, such as a method, that may include generating a two-dimensional (2D) projection image using MR imaging and determining a change between the generated 2D projection image and reference imaging information.

FIG. 9 illustrates generally a technique, such as a method, that may include generating a two-dimensional (2D) projection image using MR imaging and determining a change between the generated 2D projection image and reference imaging information. At 902, reference imaging information can be received. For example, the techniques 800A or 800B of FIG. 8A or FIG. 8B can be used to obtain reference imaging information, such as prior to treatment. In another example, a particular 3D reference image can also be generated, without requiring generation of other 3D images or aggregation of the acquired 3D images into 4D imaging information. For example, if respiration-gated therapy is to be delivered during a particular phase or amplitude of a respiration cycle, one or more 3D images can be constructed corresponding to a portion of the respiration cycle of interest, either during pre-treatment planning or intrafractionally.

At 904, a 2D projection image can be generated using techniques shown and described elsewhere herein (e.g., using a 2D MR imaging sequence with a large slice selection gradient or no slice selection gradient, or by aggregating information acquired corresponding to multiple 1D projection lines). At 906, a change between a generated 2D projection image and reference imaging information can be determined. At 908, delivery of the radiation therapy may be controlled at least in part using information indicative of the determined change.

The determined change can provide information indicative of one or more of an updated location of a target region, an anatomical feature or landmark, or a motion of the target region, anatomical feature, or landmark, as illustrative examples. In an example, the 2D MR projection image generated at 904 can include or can be related to target motion from the perspective of a radiation therapy "beam eye view" (BEV) plane. There are various ways that the target motion in the BEV plane can be extracted from a 2D MR projection image.

In one approach, a 2D/3D registration can be performed between the 2D MR projection image and 3D MR imaging information, such as in a manner similar to techniques used for registration between an X-ray projection image and a reference CT or CBCT image. Such an approach can be used, for example, to identify one or more translations that provide a match between the 2D projection image and shifted 3D MR imaging information, and the identified translation can be used as a the "change" in the context of FIG. 9 at 906 and 908 to control delivery, such as by repositioning one or more of the therapy beam output or the patient, or by modifying the therapy beam aperture. A quality of the match can be defined such as using one or more metrics, such as may include determining normalized cross-correlation or mutual information. Rotations and deformations may be included in the registration technique at the cost of simplicity and computational efficiency.

In another approach, a dimensionality reduction can be performed, such as to transform a 2D/3D registration problem into a 2D/2D registration problem. In one approach, reference projections can be extracted from 3D reference MR imaging information, in a manner similar to digitally reconstructed radiographs (DRRs) in X-ray based radiotherapy imaging. Segmentation can be used, such as to identify a target or surrounding structures such as OARs, though one more of the radiation therapy target or OARs may be masked by structures that lie in the path of the projection direction. Once the target or other structure has been segmented, a motion of the target or other structure can be identified. Such motion an also be used to predict a future location of the target.

A challenge can exist in attempting to register or otherwise compare later-acquired MR projection images with reference 3D or 4D MR imaging information. Later-acquired MR projection images may have different image quality than the reference imaging information, particularly when the reference imaging information was acquired without use of projection imaging. Registration techniques are generally more effective in comparing images having similar image quality or characteristics. The present inventors have recognized, among other things, that the reference imaging information (such as received at 902 in FIG. 9) can be acquired using MR projection imaging, such as using a rotating set of projections.

As mentioned in relation to FIG. 8A and FIG. 8B, such MR projections can be used to reconstruct a 3D MR image, such as using a tomographic reconstruction technique. In this manner, the reference 3D MR image will have similar image quality as later-acquired MR projection images. In an example, a later-acquired MR projection image can be compared directly to an acquired reference MR projection image without requiring use of 3D or 4D reference imaging information.

As mentioned above, if projection directions are rotated around the imaging subject, 4D MR reference imaging information can be compiled in manner similar to 4D-CBCT, because particular projections will generally contain different views of the anatomy of the imaging subject. Such anatomy may include landmarks such as showing a diaphragm location, or a region to be targeted by radiation. Common anatomical landmarks can then be used to bin the projections to form the 4D MRI sequence, rather than using an independent surrogate.

An acquisition duration to obtain 3D or 4D imaging information can be controlled using MR projection imaging techniques. For example, an acquisition duration can be shortened significantly such as by acquiring a more limited number of tomographic projections and using sparse tomographic reconstruction techniques such as compressed sensing or prior image compressed sensing (PICCS). An acquisition duration can also be improved such as by using parallel imaging strategies including one or more of multiple transmit or receive coils with different sensitivity profiles.

In the examples described herein, MR projections need not include projection profiles that encompass an entirety of the patient in the depth dimension along the projection direction. For example, a particular MR projection image may use a finite slice thickness encompassing an entirety of the region of interest in the depth dimension. Reducing an extent of the depth dimension can help to reduce obscuration of the region of interest (e.g., shadowing) by overlying or

Figure 10A:
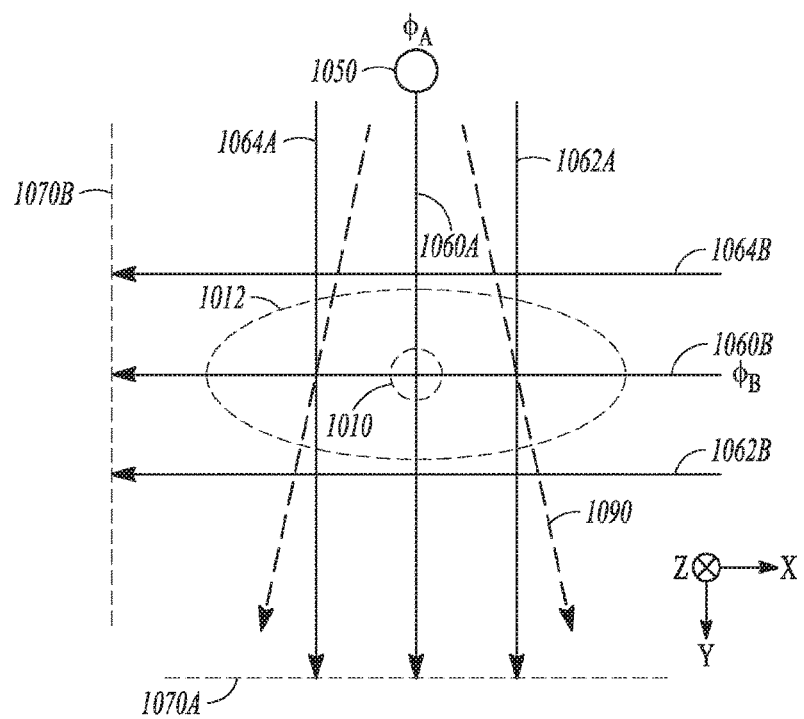
FIG. 10A illustrates generally a spatial arrangement of a radiation therapy beam orientation with respect to one or more projection directions, such as may include two projection directions oriented orthogonally to each other.

MR Projection Imaging Spatial Arrangements Such as Relative to Radiation Therapy Beam Orientation FIG. 10A illustrates generally a spatial arrangement of a radiation therapy beam orientation 1090 with respect to one or more projection directions, such as may include two projection directions oriented orthogonally to each other. In the simplest approach, an MR projection image can be acquired using a projection line orientation 1060A that coincides with the therapy beam orientation 1090, at first angular position OA. As mentioned in relation to other examples, a projection imaging plane 1070A can include information acquired using parallel projection (e.g., such as corresponding to lines 1064A and 1062A), or using a divergent projection line orientation, converging at a location 1050. The MR projection image can obtain information along the projection lines to encompass a region of interest 1012, such as including a treatment isocenter 1010. In this manner, the projection imaging plane 1070A can provide an imaging representation similar to a beam eye view (BEV) or portal image.

The configuration shown in FIG. 10A can be static, or the beam orientation and projection line orientation can be rotating together around the patient (as in the example of a gantry-mounted treatment beam output providing portal imaging). An orientation for MR projection imaging aligned with the BEV is generally a useful direction because the aperture of the therapy beam is generally shaped to provide a specified profile in the plane parallel to the projection imaging plane 1070A. Without imaging from other directions, motion of a target or imaging features may not be explicitly determined in the depth direction (e.g., Y direction), but approaches exist to estimate such motion if in-plane information indicative of target motion is available. Otherwise, additional projections can be acquired having other projection directions.

In an example, one or more MR projections perpendicular to a BEV plane may be acquired, such as at various different times. Such orthogonal images can help to obtain information missing in the depth direction (e.g., Y direction) along the first projection line orientation 1060A. For example, as shown illustratively in FIG. 10A, a second projection line orientation 1060B can be used at an orthogonal angular position AB, defining a projection imaging plane 1070B orthogonal to the first projection imaging plane 1070A. Again, parallel or divergent projection lines can be established, such as the parallel lines 1064B and 1062B shown in FIG. 10A.

Alternating or otherwise sequencing between projections parallel and perpendicular to the BEV plane can provide full depth information, at the expense of a reduced acquisition frequency of projections parallel to the BEV. The orthogonal configuration shown in FIG. 10A can simulate gantry-mounted x-ray based stereoscopic imaging. As an illustrative example, the perpendicular projections need not be acquired alternately for every BEV projection acquisition. For example, the orthogonal projection orientation may be used for acquisition only occasionally to establish or update a correlation between target motion in the BEV and motion in the depth direction.

Figure 10B:
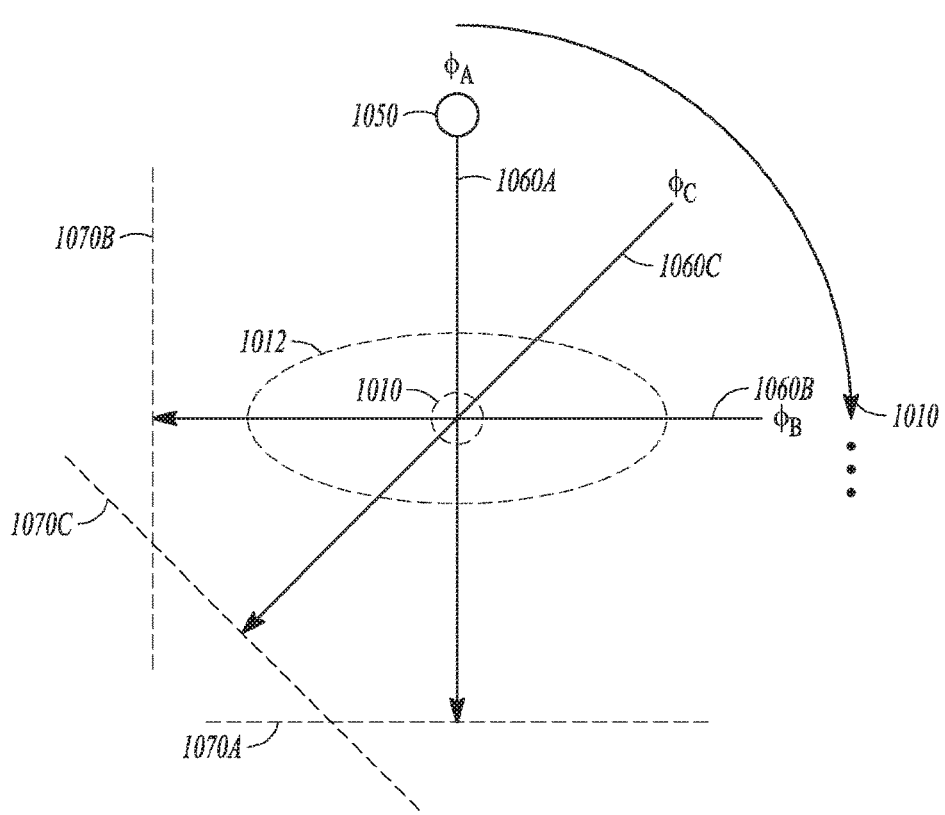
FIG. 10B illustrates generally a spatial arrangement of MR imaging projection directions, such as corresponding to projection angles spanning an arc or circle about a specified region such as a radiation therapy treatment isocenter.

FIG. 10B illustrates generally a spatial arrangement of MR imaging projection directions 1060A, 1060B, and 1060C, such as corresponding to projection angle positions $\theta_A$, $\theta_B$, $\theta_C$ spanning an arc or circle about a specified region such as a radiation therapy treatment isocenter 1010. The respective projection directions 1060A, 1060B, and 1060C can provide particular projection imaging plane orientations 1070A, 1070B, and 1070C. For rotational radiation therapy treatment deliveries, the BEV naturally rotates around the patient, such as when the radiation therapy source is mounted on a gantry. Acquired projection images can have more than one purpose. For example, as mentioned above, a particular BEV projection image can provide information indicative of a radiation therapy target position or shape from the perspective of the radiation therapy beam source. Also, if a series of projection images are acquired, a 3D tomographic MR image can be reconstructed. The MR projection orientations shown in FIG. 10B are not limited to examples where the radiation therapy beam source is rotated. For example, for radiation therapy involving one or more static therapy fields, rotating MR projections can be acquired separately from the BEV projections, such as in an alternating fashion or according to another specified imaging sequence.

Figure 10C:
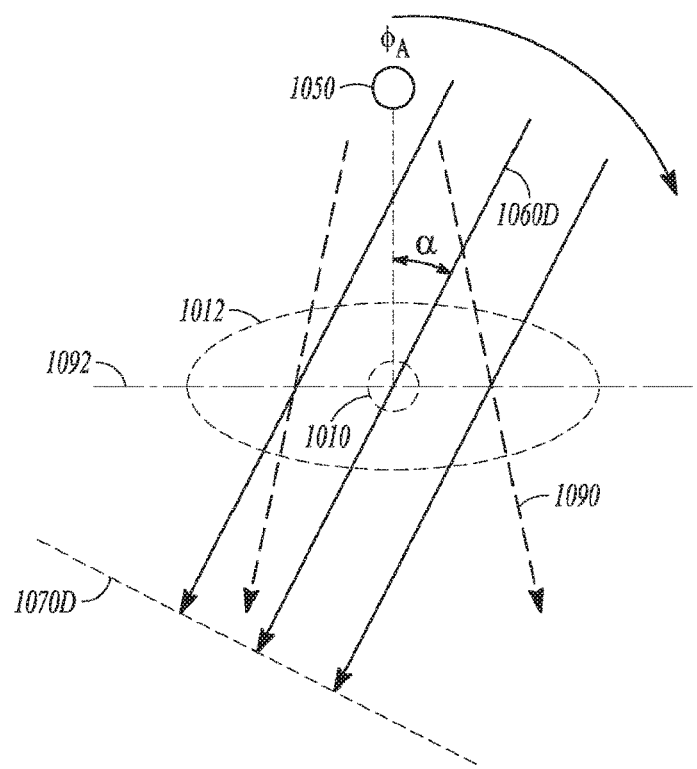
FIG. 10C illustrates generally a spatial arrangement of an MR imaging projection direction, such as oriented at a specified angle with respect to a radiation therapy beam direction

FIG. 10C illustrates generally a spatial arrangement of an MR imaging projection direction 1060D, such as oriented at a specified angle, α, with respect to a radiation therapy beam direction. The radiation therapy beam 1090 can diverge from a source location 1050, and a plane 1092 can define the BEV. By contrast with other examples, the MR imaging projection direction 1060D can be specified to capture an imaging perspective slightly different from the BEV projection, such as to obtain imaging information corresponding to a temporally-advanced BEV offset from a current BEV. Such temporally-advanced MR projection imaging can include an angle α specified to account for time lag associated with one or more of MR projection imaging acquisition, correction of the radiation therapy delivery protocol, or updating of the radiation therapy delivery protocol in response to acquired MR projection imaging. As in other examples, parallel or divergent MR projection imaging schemes can be used, and also as in other examples, the projection line orientation 1060D can be rotated relative to the radiation therapy beam orientation as the radiation therapy beam is rotated around the patient.

The advance angle α can be determined using information about one or more of a known lag duration or the angular speed of a beam-positioning gantry, as an illustrative example. A prediction technique can be applied to information acquired from the "advance BEV plane" 1070D such as to predict the most likely target position that will occur by the time the therapy output beam position catches up with the alignment of the advance BEV plane 1070D. Examples of prediction techniques can include one or more of kernel density estimation, wavelet-based techniques, or relevance vector machine (RVM) techniques. A dimensionality of the prediction problem can be reduced from three dimensions to two dimensions, because projected motion may be confined to the advance BEV plane 1070D perspective rather than having to predict target motion in a three-dimensional coordinate space.

Figure 10D:
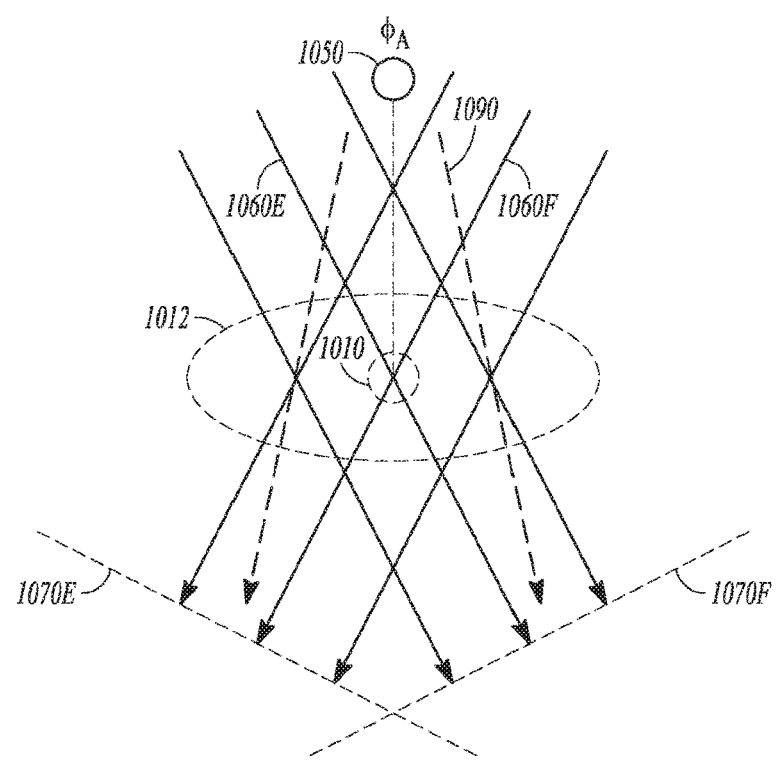
FIG. 10D illustrates generally a spatial arrangement of MR imaging projection directions, such as may be specified to provide MR projection images in a manner similar to stereoscopic X-ray imaging.

FIG. 10D illustrates generally a spatial arrangement of MR imaging projection directions 1060E and 1060F, such as may be specified to provide MR projection images in projection planes 1070E and 1070F in a manner similar to stereoscopic X-ray imaging. In the example of FIG. 10D, a projection image need not be acquired in the BEV direction, but may still be acquired using fixed orientations such as simulating room-mounted stereoscopic X-ray imaging techniques. As an illustrative example, alternating MR projections in the anterioposterior and lateral directions can be acquired such as to help locate a radiation therapy target or other anatomical features. In an example, a combination MR projection directions such as fixed orientations and rotating orientations corresponding to gantry position can be used. As an illustrative example, three or more projections can be acquired, such as in an alternating fashion, including a projection oriented to coincide with the BEV; an anterioposterior projection; and a lateral projection. Each of the projections can be selected to include a path traversing a specified region of the imaging subject, such as the treatment isocenter 1010. Such projections do not need each need to be acquired at the same imaging rate.

VARIOUS NOTES & EXAMPLES

Example 1 can include or use subject matter (such as an apparatus, a method, a means for performing acts, or a device readable medium including instructions that, when performed by the device, can cause the device to perform acts), such as can include a method for generating four-dimensional (4D) imaging information representative of a physiologic cycle of a subject, the method comprising: generating two or more two-dimensional (2D) images, the 2D images comprising projection images representative of different projection angles, and the 2D images generated using imaging information obtained via nuclear magnetic resonance (MR) imaging; assigning the particular 2D images to bins at least in part using information indicative of temporal positions within the physiologic cycle corresponding to the particular 2D images; constructing three-dimensional (3D) images using the binned 2D images; and constructing the 4D imaging information, comprising aggregating the 3D images.

In Example 2, the subject matter of Example 1 optionally includes: a physiologic cycle comprising a respiration cycle; and obtaining the two or more 2D images comprising obtaining 2D images representative of different projection angles over a duration spanning multiple respiration cycles.

In Example 3, the subject matter of any one or more of Examples 1-2 optionally includes generating two or more 2D projection images including aggregating acquired one-dimensional (1D) projection lines into a particular 2D image, the 1D projection lines oriented spatially parallel to one another.

In Example 4, the subject matter of any one or more of Examples 1-3 optionally includes generating two or more 2D projection images including aggregating acquired one-dimensional (1D) projection lines into a particular 2D image, the 1D projection lines oriented to spatially diverge from one another.

In Example 5, the subject matter of any one or more of Examples 1-4 optionally includes generating two or more 2D projection images including acquiring a 2D MR imaging slice perpendicular to a projection angle without requiring a slice selection gradient.

In Example 6, the subject matter of any one or more of Examples 1-5 optionally includes generating two or more 2D projection images including acquiring a 2D MR imaging slice perpendicular to a projection angle using a slice selection gradient defining a slice sufficiently large in depth to encompass an entirety of a radiation therapy target extent in a dimension parallel to the projection angle.

In Example 7, the subject matter of any one or more of Examples 1-6 optionally includes projection angles spanning an arc rotating about a specified central axis.

In Example 8, the subject matter of any one or more of Examples 1-7 optionally includes determining a phase of a portion of the physiologic cycle corresponding to particular 2D images; and assigning the particular 2D images to bins using information indicative of the determined phase.

In Example 9, the subject matter of any one or more of Examples 1-8 optionally includes determining an amplitude of a portion of the physiologic cycle corresponding to particular 2D images; and assigning the particular 2D images to bins using information indicative of the determined amplitude.

In Example 10, the subject matter of any one or more of Examples 1-9 optionally includes one or more of the phase or amplitude of the portion of the physiologic cycle corresponding to particular 2D images determined using a feature extracted from the particular 2D images.

In Example 11, the subject matter of Example 10 optionally includes an extracted feature corresponding to a diaphragm of an imaging subject.

In Example 12, the subject matter of any one or more of Examples 1-11 optionally includes, assigning the particular 2D images to bins using a dimensionality reduction of acquired imaging information.

In Example 13, the subject matter of any one or more of Examples 1-12 optionally includes assigning the particular 2D images to bins using a Fourier Transform of the particular 2D images.

In Example 14, the subject matter of any one or more of Examples 1-13 optionally includes constructing a 3D image from acquired 2D projection images using a tomographic image reconstruction technique.

In Example 15, the subject matter of any one or more of Examples 1-14 optionally includes constructing the 3D image from the acquired 2D projection images including performing the 3D image construction using transformed imaging information represented in a Fourier space.

In Example 16, the subject matter of any one or more of Examples 1-15 optionally includes constructing the 3D image from the acquired 2D projection images including performing the 3D image construction using a filtered back-projection technique.

In Example 17, the subject matter of any one or more of Examples 1-16 optionally includes constructing the 3D image from the acquired 2D projection images including performing the 3D image construction using a compressed sensing technique.

In Example 18, the subject matter of any one or more of Examples 1-17 optionally including constructing the 3D image from the acquired 2D projection images including performing the 3D image construction using Feldman-Davis-Kress construction.

In Example 19, the subject matter of any one or more of Examples 1-18 optionally includes constructing the 3D image from the acquired 2D projection images including performing the 3D image construction using an iterative approach.

In Example 20, the subject matter of any one or more of Examples 1-19 optionally includes providing the 4D imaging information for use in generating or adapting a radiation therapy treatment plan.

In Example 21, the subject matter of any one or more of Examples 1-20 optionally includes using the 4D imaging information to assign or determine a position of the patient prior to delivery of a radiation therapy treatment fraction.

Example 22 can include, or can optionally be combined with the subject matter of one or any combination of Examples 1-21 to include, subject matter (such as an apparatus, a method, a means for performing acts, or a machine readable medium including instructions that, when performed by the machine, that can cause the machine to perform acts), such as can include a method to control radiation therapy delivery to a subject using projection imaging, the method comprising: receiving reference imaging information; generating a two-dimensional (2D) projection image using imaging information obtained via nuclear magnetic resonance (MR) imaging, the 2D projection image corresponding to a specified projection direction, the specified projection direction including a path traversing at least a portion of an imaging subject; determining a change between the generated 2D projection image and the reference imaging information; controlling delivery of the radiation therapy at least in part using the determined change between the obtained 2D projection image and the reference imaging information.

In Example 23, the subject matter of Example 22 optionally includes, generating the 2D projection image comprising aggregating acquired one-dimensional (1D) projection lines.

In Example 24, the subject matter of Example 23 optionally includes that the specified projection direction is specified at least in part to provide 1D projection lines defined by respective paths traversing a radiation therapy treatment isocenter.

In Example 25, the subject matter of any one or more of Examples 23-24 optionally includes that the 1D projection lines are oriented to spatially diverge from one another.

In Example 26, the subject matter of any one or more of Examples 23-25 optionally includes that the directions corresponding to particular 1D projection lines are specified to converge in a location corresponding to an available position of a radiation therapy beam output.

In Example 27, the subject matter of any one or more of Examples 22-26 optionally includes that generating the 2D projection image comprises acquiring a 2D MR imaging slice perpendicular to a projection angle without requiring a slice selection gradient.

In Example 28, the subject matter of any one or more of Examples 22-27 optionally includes that generating the 2D projection image comprises acquiring a 2D MR imaging slice perpendicular to a projection angle using a slice selection gradient defining a slice sufficiently large in depth to encompass an entirety of a radiation therapy target extent in a dimension parallel to the projection angle.

In Example 29, the subject matter of any one or more of Examples 22-28 optionally includes that the specified projection direction corresponds to a present or a future radiation therapy beam direction.

In Example 30, the subject matter of any one or more of Examples 22-29 optionally includes that the specified projection direction is orthogonal to a present or a future radiation therapy beam direction.

In Example 31, the subject matter of any one or more of Examples 22-30 optionally includes that the specified projection direction is established without requiring a radiation therapy beam direction.

In Example 32, the subject matter of any one or more of Examples 22-31 optionally includes that the reference image comprises a second 2D projection image generated using earlier-acquired imaging information.

In Example 33, the subject matter of Example 32 optionally includes that the second 2D projection image is generated using four-dimensional (4D) imaging information assembled from earlier-acquired imaging information.

In Example 34, the subject matter of any one or more of Examples 22-33 optionally includes that the reference image comprises three-dimensional (3D) imaging information corresponding to earlier-acquired imaging information.

In Example 35, the subject matter of any one or more of Examples 22-34 optionally includes that the reference image comprises 4D imaging information assembled from earlier-acquired imaging information.

In Example 36, the subject matter of any one or more of Examples 22-35 optionally includes that the reference image comprises a 3D image extracted from a portion of 4D imaging information, the 4D imaging information assembled from earlier-acquired imaging information.

In Example 37, the subject matter of Example 36 optionally includes that the selected portion of the 4D imaging information comprises a specified portion of a physiologic cycle.

In Example 38, the subject matter of any one or more of Examples 22-37 optionally includes that determining the change includes using a series of two or more 2D projection images generated using imaging information obtained via nuclear magnetic resonance (MR) imaging.

In Example 39, the subject matter of any one or more of Examples 22-38 optionally includes that determining the change includes registering at least a portion of the 2D projection image with the reference image.

In Example 40, the subject matter of any one or more of Examples 22-39 optionally includes that determining the change comprises extracting a feature from the 2D projection image.

In Example 41, the subject matter of any one or more of Examples 22-40 optionally includes that determining the change includes segmenting a portion of the 2D projection image.

In Example 42, the subject matter of Example 41 optionally includes that the segmented portion of the 2D projection image comprises a perspective of a radiation therapy target.

In Example 43, the subject matter of any one or more of Examples 22-42 optionally includes that determining the change comprises triangulating between determined perspectives of the radiation therapy target segmented from two or more 2D projection images.

In Example 44, the subject matter of any one or more of Examples 22-43 optionally includes predicting a location of a radiation therapy target using the determined change and a prediction model.

In Example 45, the subject matter of Example 44 optionally includes that the prediction model includes using information indicative of target motion established at least in part using extracted perspectives of the radiation therapy target from a series of acquired 2D projection images and the determined change between at least one 2D projection image and the reference image.

Example 46 can include, or can optionally be combined with the subject matter of one or any combination of Examples 1-45 to include, subject matter (such as an apparatus, a method, a means for performing acts, or a machine readable medium including instructions that, when performed by the machine, that can cause the machine to perform acts), such as can include an imaging system, comprising: at least one processor circuit and a processor-readable storage medium, the processor readable storage medium including instructions that, when performed by the processor circuit, cause the processor circuit to generate four-dimensional (4D) imaging information representative of a physiologic cycle of a subject, including: generating two or more two-dimensional (2D) images, the 2D images comprising projection images representative of different projection angles, and the 2D images generated using imaging information obtained via nuclear magnetic resonance (MR) imaging; assigning the particular 2D images to bins at least in part using information indicative of temporal positions within the physiologic cycle corresponding to the particular 2D images; constructing three-dimensional (3D) images using the binned 2D images; and constructing the 4D imaging information, comprising aggregating the 3D images.

Example 47 can include, or can optionally be combined with the subject matter of one or any combination of Examples 1-46 to include, subject matter (such as an apparatus, a method, a means for performing acts, or a machine readable medium including instructions that, when performed by the machine, that can cause the machine to perform acts), such as can include a radiation therapy treatment system, comprising: a therapy generator; and a therapy output; a therapy controller system coupled to the radiation therapy generator and the radiation therapy output, the radiation therapy controller system comprising an imaging input, the imaging input configured to receive reference imaging information, the therapy controller system configured to: generate a two-dimensional (2D) projection image using imaging information obtained via nuclear magnetic resonance (MR) imaging, the 2D projection image corresponding to a specified projection direction, the specified projection direction including a path traversing at least a portion of an imaging subject; determine a change between the generated 2D projection image and the reference imaging information; and control delivery of the radiation therapy at radiation therapy output least in part using the determined change between the obtained 2D projection image and the reference imaging information.

Each of the non-limiting examples described in this document can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A computer-implemented method of controlling an adaptive radiation therapy delivery system, the method comprising:
   receiving reference imaging information;
   generating a two-dimensional (2D) projection image using imaging information obtained via nuclear magnetic resonance (MR) projection imaging, the 2D projection image corresponding to a specified projection direction, the specified projection direction including a path traversing at least a portion of an imaging subject;
   determining a change between the generated 2D projection image and the reference imaging information; and
   generating an updated therapy protocol for delivery of a radiation therapy at least in part using the determined change between the obtained 2D projection image and the reference imaging information.

2. The computer-implemented method of claim 1, wherein generating the 2D projection image comprises aggregating one-dimensional (1D) projection lines acquired from the MR projection imaging, wherein depth information along a given 1D projection line of the 1D projection lines is compressed into a single pixel value associated with the given 1D projection line.

3. The computer-implemented method of claim 2, wherein the 1D projection lines are oriented to spatially diverge from one another.

4. The computer-implemented method of claim 1, wherein generating the 2D projection image comprises acquiring a 2D MR imaging slice perpendicular to a projection angle without requiring a slice selection gradient.

5. The computer-implemented method of claim 1, wherein generating the 2D projection image comprises acquiring a 2D MR imaging slice perpendicular to a projection angle using a slice selection gradient defining a slice sufficiently large in depth to encompass an entirety of a radiation therapy target extent in a dimension parallel to the projection angle.

6. The computer-implemented method of claim 1, wherein the reference image comprises a 3D image extracted from a portion of 4D imaging information, the 4D imaging information assembled from earlier-acquired imaging information.

7. The computer-implemented method of claim 6, wherein the selected portion of the 4D imaging information comprises a specified portion of a physiologic cycle.

8. The computer-implemented method of claim 6, wherein the 4D imaging information is representative of a physiologic cycle, and generating the 4D imaging includes:
generating two or more projection images representative of different projection angles, the 2D images generated using imaging information obtained via nuclear magnetic resonance (MR) imaging; and
assigning the particular 2D images to bins at least in part using information indicative of temporal positions within the physiologic cycle corresponding to the particular 2D images;
constructing 3D images using the binned 2D images; and
constructing the 4D imaging information, comprising aggregating the 3D images.

9. The computer-implemented method of claim 1, wherein determining the change includes using a series of two or more 2D projection images generated using imaging information obtained via nuclear magnetic resonance (MR) imaging.

10. The computer-implemented method of claim 1, comprising predicting a location of a radiation therapy target using the determined change and a prediction model.

11. The computer-implemented method of claim 10, wherein the prediction model includes using information indicative of target motion established at least in part using extracted perspectives of the radiation therapy target from a series of acquired 2D projection images and the determined change between at least one 2D projection image and the reference image.

12. A computer-implemented method to control radiation therapy delivery to a subject using projection imaging, the method comprising:
receiving reference imaging information;
generating a two-dimensional (2D) projection image using imaging information obtained via nuclear magnetic resonance (MR) projection imaging, the 2D projection image corresponding to a specified projection direction, the specified projection direction including a path traversing at least a portion of an imaging subject;
determining a change between the generated 2D projection image and the reference imaging information; and
generating an updated therapy protocol for delivery of a radiation therapy at least in part using the determined change between the obtained 2D projection image and the reference imaging information;
wherein the reference image comprises an image extracted from a selected portion of 4D imaging information, the 4D imaging information assembled from earlier-acquired imaging information; and
wherein a selected portion of the 4D imaging information comprises a specified portion of a physiologic cycle.

13. The computer-implemented method of claim 12, wherein generating the 4D imaging includes:
generating two or more projection images representative of different projection angles, the 2D images generated using imaging information obtained via nuclear magnetic resonance (MR) imaging; and
assigning the particular 2D images to bins at least in part using information indicative of temporal positions within the physiologic cycle corresponding to the particular 2D images;
constructing 3D images using the binned 2D images; and
constructing the 4D imaging information, comprising aggregating the 3D images.

14. A radiation therapy treatment system, comprising:
a therapy controller system comprising an imaging input, the imaging input configured to receive reference imaging information, the therapy controller system configured to:
generate a two-dimensional (2D) projection image using imaging information obtained via nuclear magnetic resonance (MR) projection imaging, the 2D projection image corresponding to a specified projection direction, the specified projection direction including a path traversing at least a portion of an imaging subject;
determine a change between the generated 2D projection image and the reference imaging information; and
control delivery of the radiation therapy using the determined change between the obtained 2D projection image and the reference imaging information.

15. The radiation therapy treatment system of claim 14, wherein the therapy controller system is configured to generate the 2D projection image including aggregating one-dimensional (1D) projection lines acquired from the MR projection imaging, wherein depth information along a given 1D projection line of the 1D projection lines is compressed into a single pixel value associated with the given 1D projection line.

16. The radiation therapy treatment system of claim 14, wherein the therapy controller system is configured to generate the 2D projection image including acquiring a 2D MR imaging slice perpendicular to a projection angle without requiring a slice selection gradient.

17. The radiation therapy treatment system of claim 14, wherein the therapy controller system is configured to generate the 2D projection image including acquiring a 2D MR imaging slice perpendicular to a projection angle using a slice selection gradient defining a slice sufficiently large in depth to encompass an entirety of a radiation therapy target extent in a dimension parallel to the projection angle.

18. The radiation therapy treatment system of claim 14, wherein the reference image comprises a 3D image extracted from a portion of 4D imaging information, the 4D imaging information assembled from earlier-acquired imaging information.

19. The radiation therapy treatment system of claim 18, wherein the selected portion of the 4D imaging information comprises a specified portion of a physiologic cycle; and
the therapy controller system configured to:
generate two or more projection images representative of different projection angles, the 2D images generated using imaging information obtained via nuclear magnetic resonance (MR) imaging; and
assign the particular 2D images to bins at least in part using information indicative of temporal positions within the physiologic cycle corresponding to the particular 2D images;
construct 3D images using the binned 2D images; and
construct the 4D imaging information, including aggregating the 3D images.

20. The radiation therapy treatment system of claim 14, wherein the therapy controller system is configured to predict a location of a radiation therapy target using the determined change and a prediction model.

* * * * *